United States Patent
Faries, Jr. et al.

(10) Patent No.: US 6,768,085 B2
(45) Date of Patent: Jul. 27, 2004

(54) MEDICAL SOLUTION WARMING SYSTEM AND METHOD OF HEATING AND MAINTAINING MEDICAL SOLUTIONS AT DESIRED TEMPERATURES

(75) Inventors: Durward I. Faries, Jr., Las Vegas, NV (US); Bruce R. Heymann, Vienna, VA (US); Calvin Blankenship, Frostburg, MD (US); David Hendrix, Ashburn, VA (US)

(73) Assignee: Medical Solutions, Inc., Chantilly, VA (US)

(*) Notice: Subject to any disclaimer, the term of this patent is extended or adjusted under 35 U.S.C. 154(b) by 119 days.

(21) Appl. No.: 10/076,112

(22) Filed: Feb. 15, 2002

(65) Prior Publication Data

US 2003/0000939 A1 Jan. 2, 2003

Related U.S. Application Data

(60) Provisional application No. 60/301,829, filed on Jul. 2, 2001.

(51) Int. Cl.$^7$ ................................. H05B 1/02
(52) U.S. Cl. .................. 219/494; 219/385; 219/394; 219/395; 219/508; 219/497
(58) Field of Search .................. 219/385, 387, 219/394, 395, 398, 531, 552, 505, 508, 447.1, 448.18, 460.1, 468.2, 497, 490, 491, 494, 507; 604/114; 138/177; 165/46, 255, 257, 263, 260, 265

(56) References Cited

U.S. PATENT DOCUMENTS

| | | |
|---|---|---|
| 1,659,719 A | 2/1928 | Blake |
| 2,175,099 A | 10/1939 | Abbott |
| 2,214,215 A | 9/1940 | Watermann et al. |
| 2,576,874 A | 11/1951 | Acton |
| 2,713,112 A | 7/1955 | Mills et al. |
| 2,741,099 A | 4/1956 | Beane |

(List continued on next page.)

FOREIGN PATENT DOCUMENTS

| | | |
|---|---|---|
| DE | 37 42 927 | 7/1989 |
| DE | 197 52 578 | 6/1999 |
| WO | WO 98/45658 | 10/1998 |

OTHER PUBLICATIONS

Charles Anton, 500 miles from nowhere, It'ii give you a cold drink or a warm burger ..., Technology Update, 1993.*
Koolatron, 1997 U.S.$ PRICE LIST, Portable Electronic 12 Volt Cooler/Warmers "Cools Without Ice", Jan. 1997.*
Cahill, New Name, New Helmsman, JEMS, pp. 89, 90, and 92, Aug. 1996.*
CBI Healthcare Systems, Inc., Controlled Temperature Cabinet System, JEMS, p. 80, Mar. 1997.*
Koolatron, P–34 PC–3 Precision Control Thermoelectric Cooler/Warmer, Jan. 1998.*
Koolatron, Canadian company announces the release of a precision control unit, Aug. 1997.*

*Primary Examiner*—Tu Ba Hoang
(74) *Attorney, Agent, or Firm*—Edell, Shapiro & Finnan, LLC

(57) ABSTRACT

A temperature controlled system according to the present invention includes a housing with a compartment defined therein that includes a heating assembly with a generally 'U'-shaped heating plate and corresponding heater. The heating plate is configured to evenly distribute heat to a medical item (e.g., a medical solution container, etc.) placed thereon, while a limit switch facilitates control of heater actuation in response to placement of a medical item on the heating plate. A controller facilitates entry of desired temperatures and controls the heating assembly based on a comparison of the desired temperature with a temperature of the medical item measured by a temperature sensor. The system housing may further include a storage compartment for receiving and retaining medical items prior to being heated within the heating compartment.

90 Claims, 6 Drawing Sheets

U.S. PATENT DOCUMENTS

| | | | |
|---|---|---|---|
| 2,841,132 A | 7/1958 | Philipp | |
| 2,885,526 A | 5/1959 | Paulding | |
| 2,994,760 A | 8/1961 | Pecoraro et al. | |
| 3,051,582 A | 8/1962 | Muckler et al. | |
| 3,193,339 A | 7/1965 | Cooper | |
| 3,241,603 A | 3/1966 | Nagata | |
| 3,255,816 A | 6/1966 | Bayane et al. | |
| 3,329,202 A | 7/1967 | Birman | |
| 3,353,589 A | 11/1967 | Tope et al. | |
| 3,386,498 A | 6/1968 | Funstuck | |
| 3,485,245 A | 12/1969 | Lahr et al. | |
| 3,536,132 A | 10/1970 | Pecoraro et al. | |
| 3,590,215 A | 6/1971 | Anderson et al. | |
| 3,612,165 A | 10/1971 | Haynes | |
| 3,713,302 A | 1/1973 | Reviel | |
| 3,777,187 A | 12/1973 | Kohn | |
| 3,826,305 A | 7/1974 | Fishman | |
| 3,858,106 A | 12/1974 | Launius | |
| 3,879,171 A | 4/1975 | Tulis | |
| 4,024,377 A | 5/1977 | Henke | |
| 4,084,080 A | 4/1978 | McMahan | |
| 4,090,514 A | 5/1978 | Hinck et al. | |
| 4,167,663 A | 9/1979 | Granzow, Jr. et al. | |
| 4,189,995 A | 2/1980 | Löhr et al. | |
| 4,233,495 A | 11/1980 | Scoville et al. | |
| 4,309,592 A | 1/1982 | Le Boeuf | |
| 4,318,276 A | 3/1982 | Sato et al. | |
| 4,328,676 A | 5/1982 | Reed | |
| 4,331,859 A | 5/1982 | Thomas et al. | |
| 4,364,234 A | 12/1982 | Reed | |
| 4,407,133 A * | 10/1983 | Edmonson | 62/3.62 |
| 4,419,568 A | 12/1983 | VanOverloop | |
| 4,455,478 A | 6/1984 | Guibert | |
| 4,464,563 A | 8/1984 | Jewett | |
| 4,481,410 A * | 11/1984 | Bortnick | 219/447.1 |
| 4,495,402 A | 1/1985 | Burdick et al. | |
| 4,523,078 A | 6/1985 | Lehmann | |
| 4,605,840 A | 8/1986 | Koopman | |
| 4,657,004 A | 4/1987 | Coffey | |
| 4,678,460 A | 7/1987 | Rosner | |
| 4,680,445 A | 7/1987 | Ogawa | |
| 4,684,367 A | 8/1987 | Schaffer et al. | |
| 4,707,587 A | 11/1987 | Greenblatt | |
| 4,726,193 A | 2/1988 | Burke et al. | |
| 4,745,248 A | 5/1988 | Hayes | |
| 4,801,777 A | 1/1989 | Auerbach | |
| 4,823,554 A | 4/1989 | Trachtenberg et al. | |
| 4,832,689 A | 5/1989 | Mauerer et al. | |
| 4,874,033 A | 10/1989 | Chatelain et al. | |
| 4,894,207 A | 1/1990 | Archer et al. | |
| 4,906,816 A | 3/1990 | van Leerdam | |
| 4,910,386 A | 3/1990 | Johnson | |
| 4,934,336 A | 6/1990 | White | |
| 4,935,604 A | 6/1990 | Allen et al. | |
| 4,961,320 A | 10/1990 | Gutmann | |
| 5,013,889 A | 5/1991 | Bakke | |
| 5,061,241 A | 10/1991 | Stephens, Jr. et al. | |
| 5,061,630 A | 10/1991 | Knopf et al. | |
| 5,073,167 A | 12/1991 | Carr et al. | |
| 5,081,697 A | 1/1992 | Manella | |
| 5,106,373 A | 4/1992 | Augustine et al. | |
| 5,108,372 A | 4/1992 | Swenson | |
| 5,125,900 A | 6/1992 | Teves | |
| 5,183,994 A | 2/1993 | Bowles, Sr. et al. | |
| 5,195,976 A | 3/1993 | Swenson | |
| 5,217,064 A | 6/1993 | Kellow et al. | |
| 5,243,172 A * | 9/1993 | Hazan et al. | 219/518 |
| 5,243,833 A | 9/1993 | Coelho et al. | |
| 5,245,693 A | 9/1993 | Ford et al. | |
| 5,250,032 A | 10/1993 | Carter, Jr. et al. | |
| 5,263,323 A | 11/1993 | Maus et al. | |
| 5,263,929 A | 11/1993 | Falcone et al. | |
| 5,276,310 A | 1/1994 | Schmidt et al. | |
| 5,282,264 A | 1/1994 | Reeves et al. | |
| 5,296,684 A * | 3/1994 | Essig et al. | 219/447.1 |
| 5,297,234 A | 3/1994 | Harms et al. | |
| 5,315,830 A | 5/1994 | Doke et al. | |
| 5,333,326 A | 8/1994 | Faries, Jr. et al. | |
| 5,345,923 A | 9/1994 | Luebke et al. | |
| 5,364,385 A | 11/1994 | Harms et al. | |
| 5,381,510 A | 1/1995 | Ford et al. | |
| 5,397,875 A | 3/1995 | Bechtold, Jr. | |
| 5,399,007 A | 3/1995 | Marconet | |
| 5,408,576 A | 4/1995 | Bishop | |
| 5,424,512 A * | 6/1995 | Turetta et al. | 219/447.1 |
| 5,483,799 A | 1/1996 | Dalto | |
| 5,572,873 A | 11/1996 | Lavigne et al. | |
| 5,653,905 A | 8/1997 | McKinney | |
| 5,658,478 A * | 8/1997 | Roeschel et al. | 219/502 |
| 5,661,978 A | 9/1997 | Holmes et al. | |
| 5,729,653 A | 3/1998 | Magliochetti et al. | |
| 5,733,263 A | 3/1998 | Wheatman | |
| 5,786,568 A | 7/1998 | McKinney | |
| 5,879,329 A | 3/1999 | Ginsburg | |
| 5,910,210 A | 6/1999 | Violi et al. | |
| 5,924,289 A | 7/1999 | Bishop, II | |
| 5,961,492 A | 10/1999 | Kriesel et al. | |
| 5,977,520 A | 11/1999 | Madson, Jr. et al. | |
| 5,986,239 A | 11/1999 | Corrigan, III et al. | |
| 5,989,238 A | 11/1999 | Ginsburg | |
| 6,124,572 A | 9/2000 | Spilger et al. | |
| 6,129,702 A | 10/2000 | Woias et al. | |
| 6,174,300 B1 | 1/2001 | Kriesel et al. | |
| 6,175,099 B1 | 1/2001 | Shei et al. | |
| 6,221,045 B1 | 4/2001 | Duchon et al. | |
| 6,254,572 B1 | 7/2001 | Knipfer et al. | |
| 6,259,067 B1 | 7/2001 | Faries, Jr. et al. | |
| 6,294,762 B1 | 9/2001 | Faries, Jr. et al. | |
| 6,376,805 B2 | 4/2002 | Faries, Jr. et al. | |
| 6,384,380 B1 * | 5/2002 | Faries et al. | 219/385 |
| 6,467,953 B1 | 10/2002 | Faries, Jr. et al. | |
| 6,566,631 B2 | 5/2003 | Faries, Jr. et al. | |
| 2002/0147426 A1 | 10/2002 | Faries, Jr. et al. | |
| 2002/0158058 A1 | 10/2002 | Faries, Jr. et al. | |
| 2002/0184906 A1 | 12/2002 | Faries, Jr. | |

\* cited by examiner

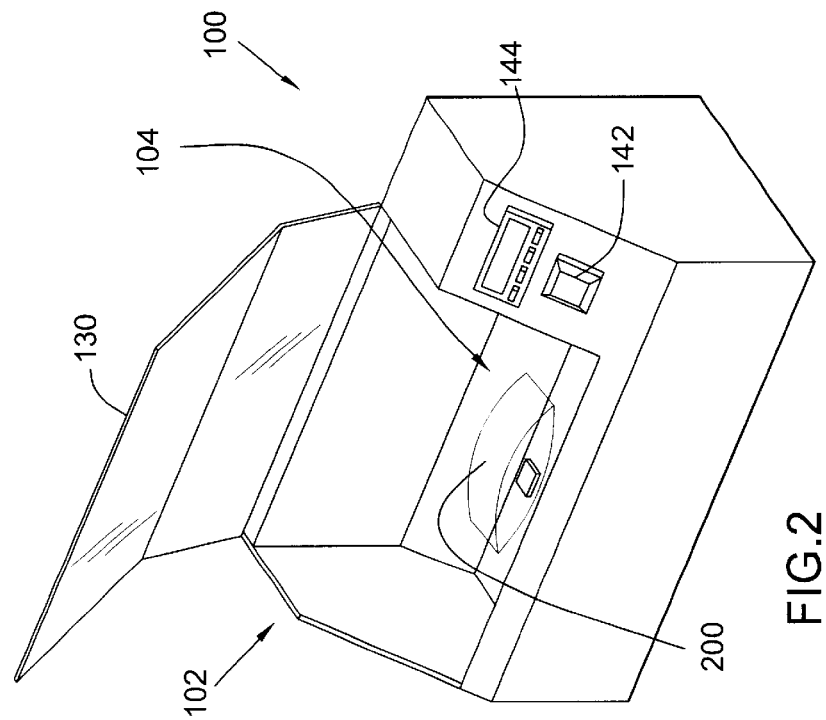
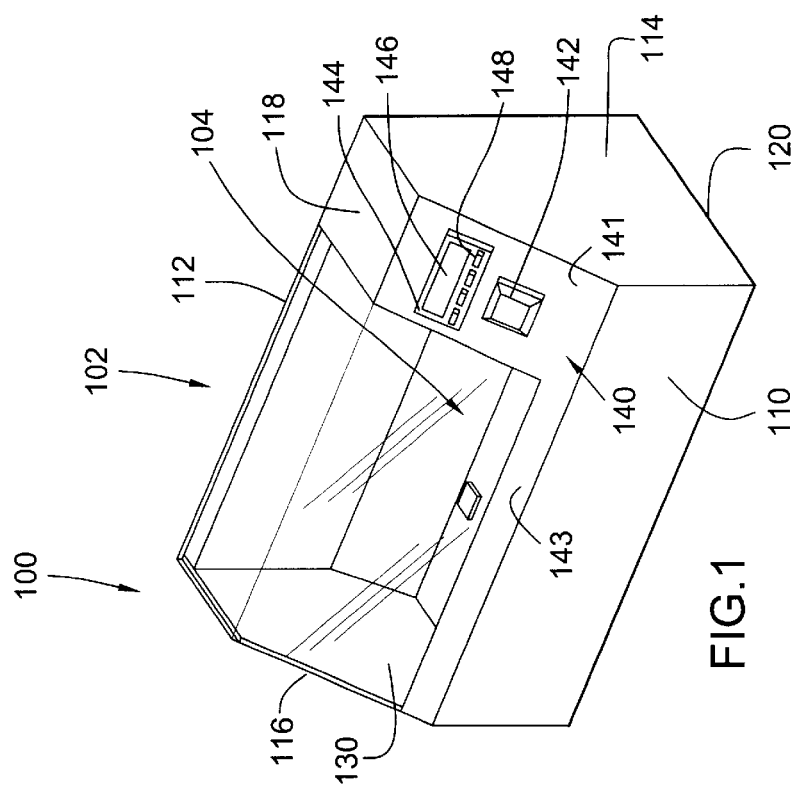
FIG. 1
FIG. 2

MEDICAL SOLUTION WARMING SYSTEM AND METHOD OF HEATING AND MAINTAINING MEDICAL SOLUTIONS AT DESIRED TEMPERATURES

CROSS-REFERENCE TO RELATED APPLICATIONS

This application claims priority from U.S. Provisional Patent Application Serial No. 60/301,829, entitled "Medical Solution Warming System and Method of Heating and Maintaining Medical Solutions at Desired Temperatures" and filed Jul. 2, 2001. The disclosure of the above-mentioned provisional application is incorporated herein by reference in its entirety.

BACKGROUND OF THE INVENTION

1. Technical Field

The present invention pertains to systems for heating medical items. In particular, the present invention pertains to a system for heating and maintaining medical solutions (e.g., bags or containers containing saline or intravenous (IV) solutions, antibiotics or other drugs, blood, etc.) at desired temperatures.

2. Discussion of Related Art

Various types of medical items require heating to a selected temperature prior to utilization in a medical procedure. In particular, medical items, such as intravenous (IV) fluid bags, are typically heated to precise temperatures to prevent thermal shock and injury from occurring during infusion of such IV fluid into a patient. In order to provide the necessary heated items for use in certain medical procedures, medical personnel typically utilize a warming system to heat items toward their operational temperatures.

The related art has provided several variations of warming systems for heating medical or other items to desired operational temperatures. For example, ovens may be disposed within operating rooms to heat items to desired temperatures. Further, U.S. Pat. No. 4,419,568 (Van Overloop) discloses a wet dressings heater having a base with side walls defining a cavity, and an insert connected to the base and defining at least one recess in the cavity for receiving wet dressings. A heater has an electrical heating element in close proximity to the insert recess for heating the wet dressings, while the temperature of the heating element is controlled in a desired temperature range for those wet dressings.

U.S. Pat. No. 4,495,402 (Burdick et al) discloses a warmer for heating wet dressings and other articles disposed within a heating and storage compartment. The articles are arranged within the compartment in stacked relation and disposed on a plate that is supplied with thermal energy from a heater. The plate includes a center aperture whereby a first thermal sensor is disposed in the aperture in contact with a bottommost article. Control circuitry is disposed beneath the plate to control the heater to maintain temperature of the bottommost article at a desired level based on the temperatures sensed by the first thermal sensor and a second thermal sensor responsive to heater temperature.

U.S. Pat. No. 5,408,576 (Bishop) discloses an intravenous fluid warmer having a cabinet structure to accommodate a plurality of intravenous fluid bags. A temperature sensor and pad of heating filaments are disposed within the cabinet structure, whereby the temperature sensor enables automatic temperature regulation of the pad of heating filaments to heat the intravenous fluid bags. The heating filaments are covered by a rubber layer to prevent melting of the bags during heating. A temperature indicator disposed on the cabinet structure permits a user to ascertain when a desired temperature is attained, whereby an intravenous fluid bag is removed from the intravenous fluid warmer via an opening defined in a side of the cabinet structure.

U.S. Pat. No. 5,986,239 (Corrigan, III et al.) discloses a conductive warmer for flexible plastic bags. The warmer includes a heat-conducting member of thermally conductive material having a plurality of fins which are parallel and spaced apart to define a plurality of bag-receiving compartments. The fins are connected to a back portion of the heat-conducting member to which a heating element is attached in a heat-exchanging relationship. The heating element conducts heat through the back portion and fins of the heat-conducting member to the bags.

The warming systems described above suffer from several disadvantages. In particular, ovens typically do not have a high degree of accuracy or control, thereby enabling use of items having temperatures incompatible with a medical procedure and possibly causing injury to a patient. Further, ovens or other warming systems employed in the operating room generally require a substantial time interval to heat items to desired temperatures. This either delays the medical procedure or requires the additional task or preheating the items well in advance of commencing the procedure. The Burdick et al and Bishop warmers employ heaters that generally contact a particular portion of an article being heated, thereby heating articles in an uneven manner and enabling formation of hot spots. Moreover, the Burdick et al, Bishop, Corrigan, III et al and Van Overloop warming systems employ a heating element covering a substantial portion of a conducting member, thereby increasing system costs and power usage. In addition, the above described systems do not control operation based on detection of the presence of items placed within the systems. This enables the systems to operate absent items placed therein, thereby needlessly consuming power and facilitating potential damage to system heating or other components.

OBJECTS AND SUMMARY OF THE INVENTION

Accordingly, it is an object of the present invention to rapidly heat a medical item to a desired temperature in preparation for use of that medical item in a medical procedure.

It is another object of the present invention to heat a medical item to a desired temperature by uniformly distributing heat about the medical item, thereby avoiding creation of "hot spots" and "cold spots".

Yet another object of the present invention is to directly measure a temperature of a medical item being heated to effectively control heating of the medical item to the desired temperature.

Still another object of the present invention is to automatically enable a heater in a warming system in response to the presence of the medical item within the warming system.

A further object of the present invention is to evenly distribute heat about a medical item within a warming system by conducting heat through a heating plate that at least partially surrounds the medical item.

Yet another object of the present invention is to facilitate loading of a plurality of medical items within a warming system housing for heating to desired temperatures prior to use in medical procedures.

The aforesaid objects may be achieved individually and/or in combination, and it is not intended that the present invention be construed as requiring two or more of the objects to be combined unless expressly required by the claims attached hereto.

According to the present invention, a temperature controlled system includes a system housing with a compartment defined therein. The compartment includes a heating assembly with a generally 'U'-shaped heating plate and corresponding heater. The heating plate is configured to evenly distribute heat to a medical item (e.g., a medical solution container, etc.) placed thereon, while a limit switch facilitates control of power to the heater. The limit switch is typically positioned near a bearing surface of the heating plate to enable a limit switch arm to directly contact medical solution containers placed on the heating plate. The limit switch facilitates heater actuation in response to placement of a medical item on the heating plate. A temperature sensor measures the temperature of solutions disposed within the housing compartment, and is preferably positioned on the limit switch arm to directly contact a medical solution container. A system controller facilitates entry of desired temperatures and controls the heating assembly based on a comparison of the desired temperature with the temperature measured by the temperature sensor. The controller includes a display for indicating the solution temperature. In one embodiment of the present invention, the system housing includes a heating compartment for heating medical solution containers and a storage compartment for receiving and retaining medical solution containers prior to being heated within the heating compartment.

Thus, the present invention overcomes the aforementioned problems and provides several advantages. For example, the warming system of the present invention distributes heat evenly to one or more medical items of varying shapes and sizes, thereby ensuring rapid and relatively uniform heating and the elimination of potential "hot spots" or "cold spots" for the items. Further, the warming system of the present invention provides a temperature sensor that directly measures the temperature of medical items disposed within the system, thereby providing an accurate temperature indication of those medical items and enhanced temperature control. Moreover, the present invention includes a switch to autonomously enable the heater in response to a medical item being disposed on the heating plate. This ensures that heating within the system only occurs when medical items are disposed on the heating plate so as to render the system energy efficient and promote longevity of the heating element.

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

BRIEF DESCRIPTION OF THE DRAWINGS

FIG. 1 is a view in perspective of a temperature controlled system in accordance with the present invention.

FIG. 2 is a view in perspective of the system of FIG. 1 with a medical solution container placed therein.

DETAILED DESCRIPTION OF THE PREFERRED EMBODIMENTS

Figure 4:
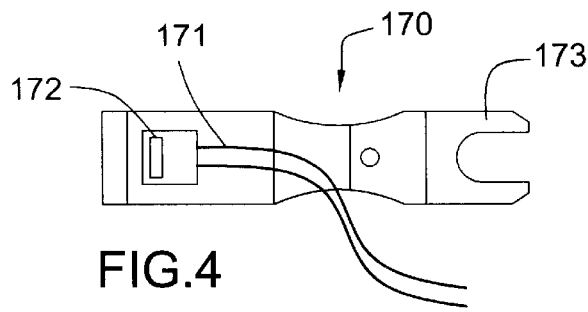
FIG. 4 is a top view in plan of a limit switch arm employed by the system of FIG. 1.

A temperature controlled system for heating and maintaining medical solutions (e.g., bags or bottles containing saline or intravenous (IV) solutions, antibiotics or other drugs, blood, etc.) at desired temperatures is illustrated in FIG. 1. It is noted that, while the figures illustrate medical solution containers being heated within the system, the system can accommodate the heating of a variety of different medical items. Specifically, temperature controlled system 100 includes a housing 102 and a heating assembly 104 disposed within a housing compartment to heat medical solutions. The housing includes a front wall 110, a rear wall 112, side walls 114, 116, a top wall 118, a bottom wall 120 and a front panel 140 that collectively define the housing interior. A door 130 is disposed on the housing to cover a housing open portion that facilitates placement and removal of items within the housing as described below. Front and rear walls 110, 112 are substantially rectangular and are attached to and extend between side walls 114, 116. Front wall 110 has a height substantially less than that of rear wall 112. Bottom wall 120 is substantially rectangular and is attached to the front, rear and side wall bottom edges. Top wall 118 is substantially rectangular and is attached to rear wall 112 and side wall 114. The top wall extends from side wall 114 for a distance substantially less than the distance between the side walls to partially define the housing open portion between the top wall and side wall 116. The top wall further extends from rear wall 112 for a distance less than the distance between the front and rear walls. Side walls 114, 116 are generally rectangular with respective truncated upper front corner sections. The truncated section of side wall 114 includes an angled edge that extends between front wall 110 and top wall 118. The truncated section of side wall 116 includes a similarly angled edge.

Front panel 140 includes a control panel 141 and a projection 143. The control panel is substantially rectangular and is attached to top wall 118, front wall 110 and the angled edge of side wall 114. The control panel has a transverse dimension similar to that of the top wall and is oriented at an angle toward rear wall 112 similar to that of the angled side wall edge. Projection 143 is substantially rectangular and is attached to front wall 110, a control panel lower section and side wall 116. The projection extends from the front wall toward the rear wall for a slight distance and is oriented at an angle similar to that of control panel 141. The open area between control panel 141, side wall 116 and projection 143 defines the remaining area of the housing open portion.

A control assembly is typically disposed on control panel 141. The control assembly includes a power switch 142 and a controller 144 to indicate solution temperature and control operation of the system as described below. Controller 144 includes a display 146 (e.g., LED or LCD) and a plurality of input devices or buttons 148. The input devices are manipulable by a user to enable entry of a desired or set point temperature for a medical solution container placed within the housing compartment. Display 146 typically displays the measured temperature of the solution and may further be directed, via the input devices, to display the desired or set point temperature. It is to be understood that the terms "top", "bottom", "side", "front", "rear", "upper", "lower", "vertical", "horizontal", "height", "width", "length" and the like are used herein merely to describe points of reference and do not limit the present invention to any specific orientation or configuration. The system housing and components (e.g., walls, panels, etc.) may be of any size, shape or configuration suitable for operation of the system and may be constructed of any suitable materials.

Door 130 provides access to the housing compartment and covers the housing open portion. The door includes an upper section that is configured to cover the housing open portion defined between top wall 118 and side wall 116, and a lower section configured to cover the housing open portion defined between control panel 141, projection 143 and side wall 116. Thus, the door lower section is typically angled in a manner similar to that of the control panel and projection. The door upper and lower sections maybe pivotally connected or may be joined at an angle to accommodate the angled configuration of the housing front panel. Door 130 is preferably pivotally connected to rear wall 112 and opens away from the front panel and top wall to expose the housing compartment and facilitate placement and removal of medical solution containers within the system. A system with door 130 in an open state and a medical solution container 200 placed within the housing interior compartment is illustrated, by way of example only, in FIG. 2. The door may be of any size or shape and may open in any direction or manner with respect to the housing suitable for operation of the system. Door 130 may further include a handle (not shown) disposed at any suitable location (e.g., toward a door side or bottom edge). The handle may be implemented by any conventional or other type of handle. Alternatively, the door may include a latching mechanism of any conventional or other configuration that facilitates manual or automatic opening of the door via an unlatching activation member (e.g., a button located on the upper front panel of the housing that is depressed to unlatch the door). The door is typically constructed of a transparent material, such as glass or plexiglass, to allow viewing of the housing compartment when the door is in a closed state. However, the door may be constructed of any suitably sturdy materials, with a portion of the door preferably including a window or other viewing area.

Figure 3:
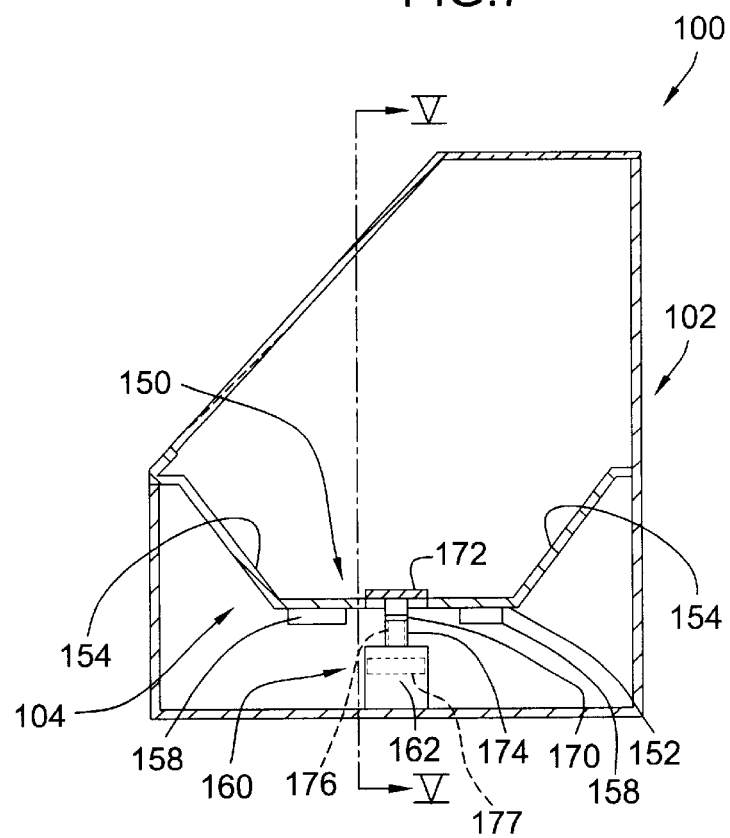
FIG. 3 is a side view in partial section of the system of FIG. 1.

An exemplary heating assembly employed by the present invention is illustrated in FIG. 3. Specifically, heating assembly 104 includes a heating plate 150 and a heater 158. Heating plate 150 is typically located at the bottom of the housing compartment and includes a bottom wall 152 and side walls 154. The heating plate bottom and side walls are each substantially rectangular with the side walls extending at an angle from opposing bottom wall longer dimensioned side edges toward the interior surfaces of the housing front and rear walls to form a generally 'U'-shaped heating plate configuration. The heating plate bottom wall typically receives medical solution containers, while the heating plate bottom and side walls conduct heat from heater 158 to provide uniform heat distribution to those containers. Thus, heat is simultaneously applied to three sides of the container. The heating plate is preferably constructed of a thermally conductive material, while heat is conducted from one plate wall in contact with the heater to the remaining plate walls to distribute heat to the medical solution container placed on the heating plate.

Heater 158 is disposed on the underside of heating plate bottom wall 152. The heater applies heat to bottom wall 152 which, in turn, distributes heat to the plate side walls and medical solution container placed on the heating plate. This arrangement facilitates rapid heating of the medical item to a desired temperature which is especially advantageous during employment of the system in time critical situations, such as in an operating room. For example, the system may heat items to a desired temperature in the approximate range of 80° F. to 150° F. within a short time interval, generally within one hour (e.g., the particular time interval depends on various factors, such as initial item temperature, room temperature, selected desired temperature, etc.). Controller 144 (FIG. 1) is electrically coupled to the heater to control the heater in response to a measured solution temperature as described below. Heater 158 is generally rectangular and preferably configured to cover a portion of the heating plate bottom wall. The heater is typically implemented by a conventional etched foil silicon rubber heating pad, and is attached to the underside of bottom wall 152 via a pressure sensitive or other type of adhesive. The heater may alternatively be of any quantity (e.g., at least one), shape or size, and may include any configuration (e.g., strips, bars, segments, etc.) that covers the entirety or any portion of the heating plate. In addition, the heater may be implemented by any conventional or other type of heater or heating element (e.g., heating coils, etc.) that may be disposed on the heating plate at any suitable locations.

The heating assembly further includes a temperature sensor 172 and a limit switch 160 that controls heater 158 in response to detection of the presence of medical solution containers on the heating plate. The temperature sensor is typically in direct contact with a medical solution container to provide a highly accurate temperature indication for the medical solution contained within that container. Temperature sensor 172 is positioned above the bearing surface of heating plate bottom wall 152 as described below, and directly measures the temperature of a medical solution container placed on the heating plate. The temperature sensor is preferably implemented by a conventional resistive temperature device (RTD) (e.g., 1,000 Ohm RTD). However, the temperature sensor may be implemented by any conventional or other type of temperature sensor, and maybe disposed at any suitable location on the heating plate or within the compartment.

Referring to FIGS. 3–4, limit switch 160 controls heater 158 in response to placement and removal of medical solution containers on the heating plate. Specifically, the limit switch is typically implemented in the form of a pressure type switch that enables or disables the heater in response to detection of pressure (e.g., the weight of a container) applied to a portion of the heating plate. However, the limit switch may alternatively be configured in any manner suitable for operation of the system. The limit switch includes a housing 162 and an arm 170. The limit switch housing is disposed beneath the heating plate bottom wall and includes a post or support member 174 extending from the housing top surface toward the heating plate. Arm 170 is attached in a cantilevered manner to support member 174. The arm includes a receptacle 173 disposed at the arm proximal end to receive the support member and facilitate attachment of the arm thereto. Temperature sensor 172 is mounted on arm 170 toward the arm distal end with wiring 171 extending from the sensor to controller 144 (FIG. 1) as described below. The arm extends from the support member along the underside of the heating plate bottom wall to align sensor 172 with an opening (not shown) defined in the heating plate bottom wall. The bottom wall opening provides temperature sensor 172 with access to a medical solution container placed on the heating plate. The limit switch arm is constructed of a resilient material that biases the arm toward the heating plate and enables the arm to move between that plate and the limit switch housing. The arm bias further forces the temperature sensor against a medical solution container placed on the heating plate, thereby facilitating an accurate temperature measurement. A contact member 176 (FIGS. 3 and 5–6) is disposed on housing 162 coincident a distal portion of the limit switch arm and extends into the limit switch housing via an opening (not shown) defined in that housing. The contact member is typically directly attached to or resiliently biased toward the limit switch arm to enable movement of the contact member into or out of the limit switch housing in response to flexing of the limit switch arm.

The contact member is configured to actuate switch circuitry 177 disposed within the limit switch housing. In particular, the limit switch arm flexes toward the limit switch housing in response to pressure applied to the arm from a medical solution container placed on the heating plate. Contact member 176 is subsequently urged into housing 162 and interfaces control circuitry 177. This motion results in actuation of the switch circuitry and effectively closes switch 160, thereby enabling heater 158. When a container is removed from the heating plate, arm 170 is biased toward the heating plate bottom wall with the contact member being withdrawn from the switch circuitry. This motion effectively results in disablement of the switch circuitry and effectively opens switch 160, thereby disabling the heater.

Figure 6:
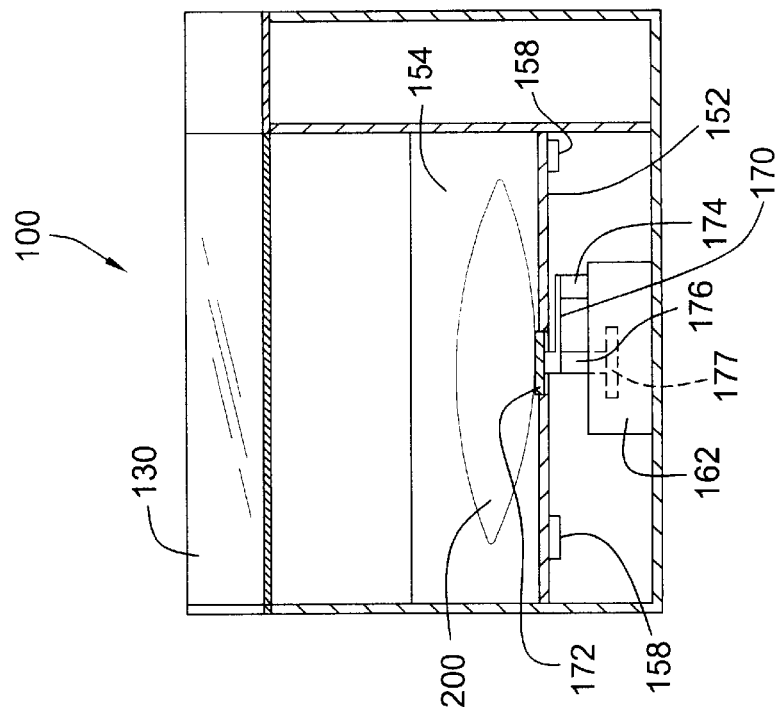
FIG. 6 is a front view in partial section of the system of FIG. 3 taken along lines V—V where the system includes a medical solution container placed therein.
Figure 5:
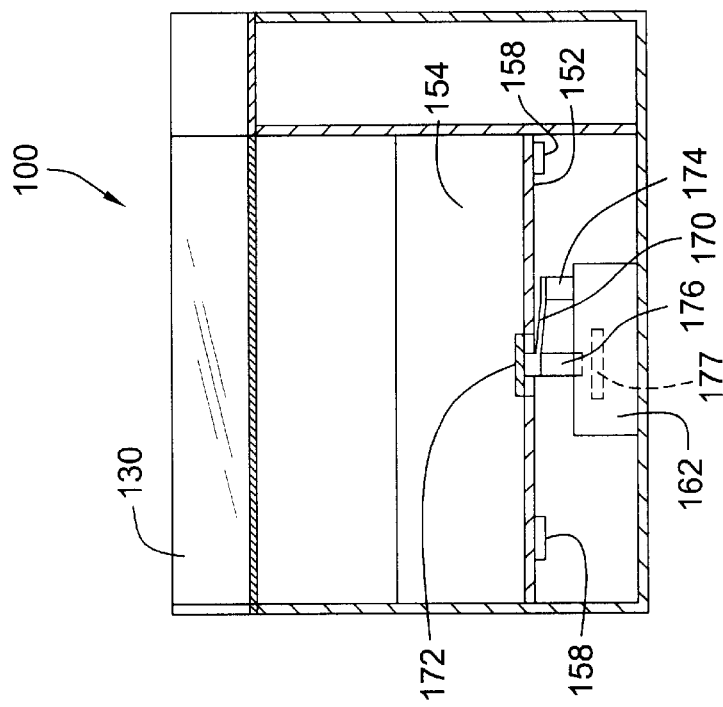
FIG. 5 is a front view in partial section of the system of FIG. 3 taken along lines V—V.

The limit switch controls the heater in response to detection of the presence of a medical solution container on the heating plate as illustrated, byway of example only, in FIGS. 5–6. Specifically, when no medical solution container is present on the heating plate, limit switch arm 170 is biased toward the heating plate (FIG. 5) with contact member 176 withdrawn from limit switch housing 162 (e.g., the contact member is withdrawn from the switch circuitry). The limit switch is effectively in an open state, thereby disabling heater 158 as described above. When a medical solution container 200 is placed within the compartment (FIG. 6), the container contacts sensor 172 and forces limit switch arm 170 to flex toward limit switch housing 162. The flexion of the limit switch arm forces contact member 176 to extend within the limit switch housing to actuate switch circuitry 177 and effectively close switch 160, thereby enabling the heater as described above. Removal of container 200 from the compartment restores the limit switch arm to the initial biased position (FIG. 5), thereby disabling the heater.

Figure 7:
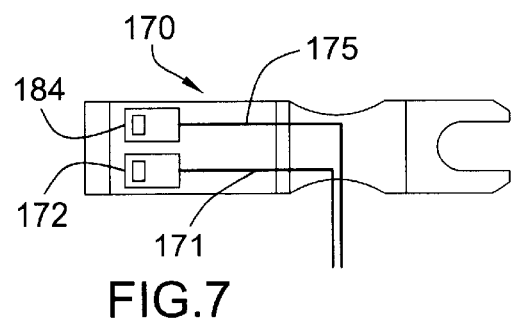
FIG. 7 is a top view in plan of an alternative embodiment of a limit switch arm employed by the system of FIG. 1.

Temperature sensor 172 is disposed on arm 170 and provides a temperature measurement to controller 144 (FIG. 1) for control of the heater as described above. A temperature cut-out switch may further be employed by the heating assembly and disposed on arm 170 as illustrated in FIG. 7. Cut-out switch 184 basically disables current to heater 158 in response to a temperature measurement exceeding a temperature threshold. In other words, the cut-out switch disables the heater in response to detection of excessive heater temperatures. The cut-out switch may be implemented by any conventional switching type or limiting devices, such as a high limit thermostat, and may be disposed at any suitable location. Specifically, limit switch arm 170 includes temperature sensor 172 and cut-out switch 184. Temperature sensor 172 is disposed toward the limit switch arm distal end, while cut-out switch 184 is disposed adjacent sensor 172 and serves to disable operation of the heater in response to detection of excessive heater temperatures. Wiring 171,175 respectively extend from temperature sensor 172 and cut-out switch 184 to the system control circuitry (FIG. 8A) to facilitate control of system operation in response to conditions detected by the sensor and switch. Alternatively, a sensor element may be employed that performs the functions of each of the temperature sensor and cut-out switch. The cut-out switch may be disposed at any suitable locations on the arm or within the housing compartment along with, or independent of, the temperature sensor.

The cut-out switch may alternatively be implemented by an additional temperature sensor 186 (FIG. 8B) to facilitate disablement of the heater in response to excessive heater temperatures. In particular, temperature sensor 186 is substantially similar to temperature sensor 172 and may be disposed on arm 170 in substantially the same manner described above for cut-out switch 184. Temperature sensor 186 measures the temperature of a container placed on the heating plate and provides a temperature signal to controller 144 via appropriate wiring. The controller disables power to the heater in response to the temperature signal indicating a temperature in excess of a predetermined threshold. Temperature sensor 186 may be disposed at any suitable location on the arm or within the housing compartment along with, or independent of, temperature sensor 172.

Figure 8A:
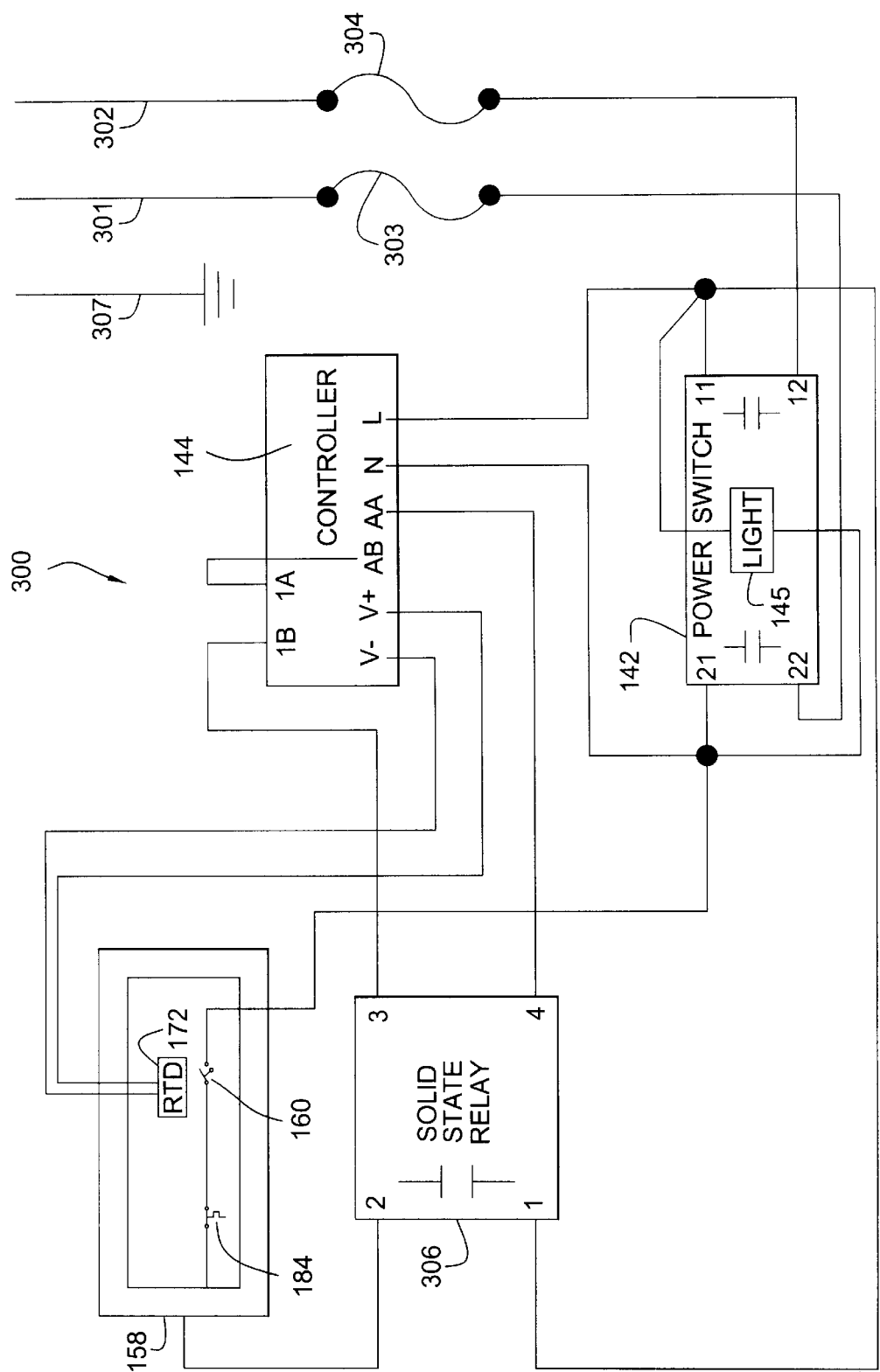
FIG. 8A is an electrical schematic diagram of an exemplary control circuit for the system of FIG. 1 employing a cut-out switch to control the heater in response to excessive heater temperatures.

An exemplary system control circuit employing the cut-out switch to facilitate disablement of the heater in response to excessive heater temperatures is illustrated in FIG. 8A. Specifically, a control circuit 300 includes power conductors 301, 302, a ground 307, power switch 142, controller 144, a solid state relay 306, high temperature cut-out switch 184, limit switch 160, heater 158 and temperature sensor 172. Power conductors 301,302 each include a respective fuse 303, 304 (e.g., a conventional two amp fuse) that is arranged in series with power switch 142 to prevent power surges from damaging the switch and circuitry. Power switch 142 controls power to the circuitry and is connected to the controller, relay and heater. The power switch may include a light 145 to illuminate the switch. Controller 144 is further connected to solid state relay 306 and temperature sensor 172. The controller controls power applied to the heater via relay 306 in accordance with a comparison of a temperature measured by temperature sensor 172 and a desired temperature entered into the controller by a user. In particular, controller 144 receives temperature signals from temperature sensor 172 indicating the temperature of a medical solution container in contact with the sensor (i.e., the container disposed on the heating plate surface). In response to the temperature measured by sensor 172 being equal to or exceeding a desired temperature entered by a user, the controller disables power to the heater via solid state relay 306. Conversely, when the temperature measured by temperature sensor 172 is below the desired temperature, the controller enables power to the heater via the solid state relay.

Limit switch 160 is connected between power switch 142 and heater 158 and controls power to the heater in accordance with the presence of a medical solution container within the system as described above. Temperature cut-out switch 184 is similarly connected between the power switch and heater to disable the heater in response to detecting a heater temperature in excess of a predetermined threshold as described above. Thus, the limit and cut-out switches 160, 184 directly control power to the heater irrespective of relay 306. In other words, these switches override the controller and relay to disable power to the heater in response to detection of the absence of a medical solution container on the heating plate and excess heater temperatures, respectively. Control circuit 300 may alternatively be implemented by any conventional circuitry components performing the above-described functions.

Figure 8B:
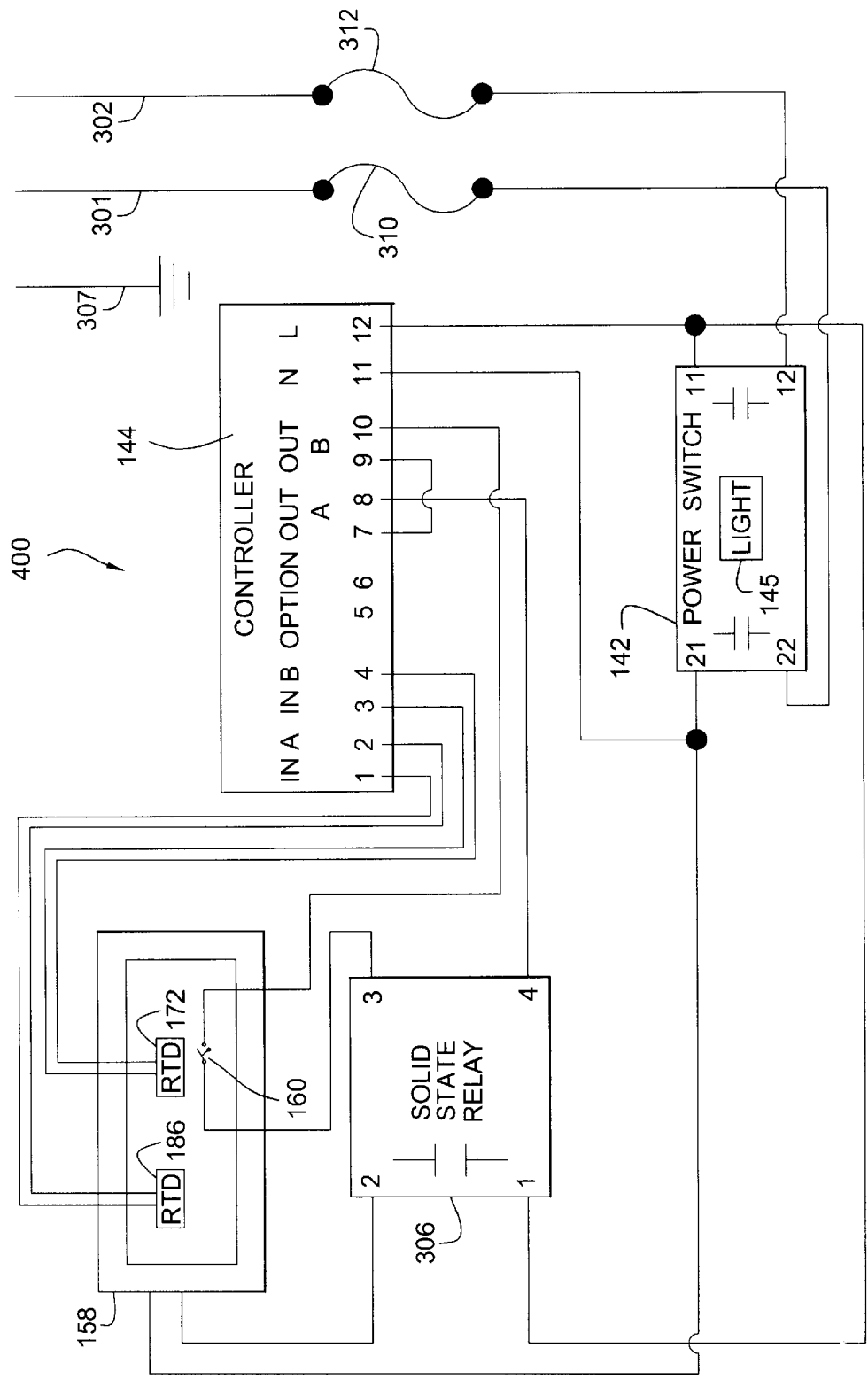
FIG. 8B is an electrical schematic diagram of an exemplary control circuit for the system of FIG. 1 employing an additional temperature sensor to facilitate control of the heater in response to excessive heater temperatures.

An exemplary system control circuit employing an additional temperature sensor to facilitate disablement of the heater in response to excessive heater temperatures is illustrated in FIG. 8B. Specifically, a control circuit 400 includes power conductors 301, 302, ground 307, power switch 142, solid state relay 306, limit switch 160, heater 158 and temperature sensor 172, each as described above. The circuitry further includes controller 144 and additional temperature sensor 186. Controller 144 is substantially similar to the controller described above and further accommodates temperature sensor 186 to facilitate control of the heater in response to excessive heater temperatures as described below. Power conductors 301, 302 each include a respective fuse 310, 312 (e.g., a conventional 1.5 amp fuse) that is arranged in series with power switch 142 to prevent power surges from damaging the switch and circuitry. Power switch 142 controls power to the circuitry and is connected to the controller, relay and heater. The power switch may include a light 145 to illuminate the switch. Controller 144 is further connected to solid state relay 306 and temperature sensors 172, 186. The controller controls power applied to the heater via relay 306 in accordance with a comparison of a temperature measured by temperature sensor 172 and a desired temperature entered into the controller by a user. In particular, controller 144 receives temperature signals from temperature sensor 172 indicating the temperature of a medical solution container in contact with the sensor (i.e., the container disposed on the heating plate surface). In response to the temperature measured by sensor 172 being equal to or exceeding a desired temperature entered by a user, the controller disables power to the heater via solid state relay 306. Conversely, when the temperature measured by temperature sensor 172 is below the desired temperature, the controller enables power to the heater via the solid state relay.

Limit switch 160 is connected between controller 144 and solid state relay 306 and facilitates control of the heater in accordance with the presence of a medical solution container within the system. Basically, the limit switch enables the solid state relay to control power to the heater in accordance with control signals generated by the controller. When a medical solution container is present on the heating plate, the limit switch is in a closed state as described above. Accordingly, the connection between the controller and relay is enabled to facilitate control of the heater in accordance with control signals generated by the controller. Conversely, when a medical solution container is removed or absent from the heating plate, the limit switch is in an open state as described above. Thus, the connection between the controller and relay is disabled to prevent operation of the heater.

Temperature sensor 186 is connected to the controller to facilitate disablement of the heater in response to detecting a heater temperature in excess of a predetermined threshold as described above. Basically, temperature sensor 186 provides a temperature indication of the solution container to controller 144. The controller disables power to the heater via relay 306 in response to the measured temperature exceeding a predetermined threshold as described above. Control circuit 400 may alternatively be implemented by any conventional circuitry components performing the above-described functions.

Operation of the temperature controlled system is described with reference to FIGS. 1–7, 8A and 8B. Initially, a user selects a medical solution (e.g., a bag or bottle containing saline or IV solutions, antibiotics or other drugs, blood, etc.) for heating within the housing compartment and determines an appropriate temperature for the solution. The user subsequently activates power switch 142 and pivots door 130 (e.g., via a handle disposed on the door) outward from the housing to an open state. The selected solution is placed on heating plate bottom wall 152 within the housing compartment, and the door is subsequently pivoted toward the housing to a closed state. The desired temperature for the medical solution is entered into controller 144 via input devices or buttons 148. In response to placement of the medical solution container on the heating plate bottom wall, the container engages temperature sensor 172 and causes limit switch arm 170 to flex toward limit switch housing 162. The flexing of the limit switch arm forces contact member 176 into the limit switch housing to close switch 160 and enable the heater as described above. The controller receives signals from temperature sensor 172 and controls solid state relay 306 accordingly to enable or disable power to heater 158. The heater applies heat to the heating plate bottom wall, while heating plate side walls 154 conduct heat from bottom wall 152 to evenly distribute heat to the medical solution container. Cut-out switch 184 and/or temperature sensor 186 may be employed to facilitate disablement of the heater in response to excessive heater temperatures as described above.

Controller 144 displays the temperature of the container as measured by temperature sensor 172, and may alternatively display the desired or set point temperature entered by the user. When the medical solution has attained the desired temperature, the door is pivoted to an open state as described above and the heated medical solution container is removed from the housing compartment. The door is subsequently returned to a closed state. In response to removal of the container from the heating plate bottom wall, the limit switch arm is biased toward the heating plate, thereby opening the limit switch and disabling the heater as described above. Further, an additional medical solution container may replace the removed container within the housing compartment for heating by the system. The system preferably accommodates a single medical item, however, any quantity of medical items may be disposed within the compartment for heating by the system.

Figure 9:
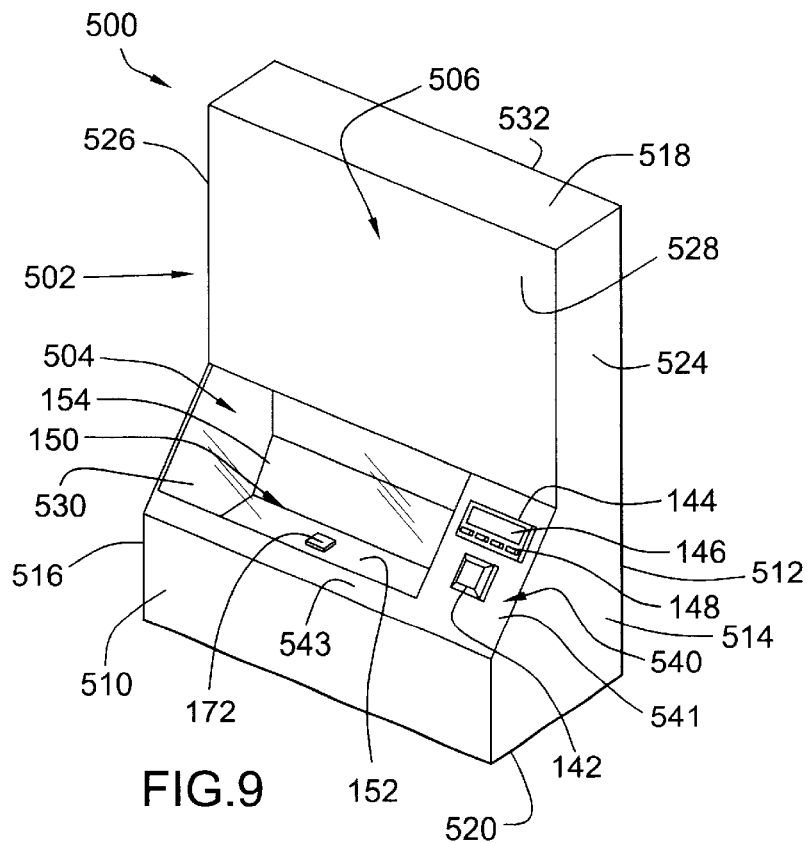
FIG. 9 is a view in perspective of an alternative embodiment of the temperature controlled system of FIG. 1 in accordance with the present invention.

An alternative embodiment of the temperature controlled system according to the present invention is illustrated in FIG. 9. Initially, the alternative system is substantially similar to system 100 described above, except that the alternative system housing is configured to accommodate a plurality of medical solution containers or other items. Specifically, system 500 includes a housing 502 including a heating compartment 504 and a storage compartment 506 disposed above the heating compartment. The heating compartment is substantially similar to system 100 described above and includes a front wall 510, a rear wall 512, side walls 514, 516, a bottom wall 520 and a front panel 540 that collectively define the heating compartment interior. A door 530 is disposed on the housing to cover a heating compartment open portion that facilitates placement and removal of items within the heating compartment as described below. Front and rear walls 510, 512 are substantially rectangular and are attached to and extend between side walls 514, 516. Front wall 510 has a height substantially less than that of rear wall 512. Bottom wall 520 is substantially rectangular and is attached to the bottom edges of the heating compartment front, rear and side walls. Side walls 514, 516 are generally rectangular with respective truncated upper front corner sections. The truncated section of side wall 514 includes an angled edge that extends from front wall 510 toward the storage compartment. The truncated section of side wall 516 includes a similarly angled edge.

Front panel 540 includes a control panel 541 and a projection 543. The control panel is substantially rectangular and is attached to front wall 510 and the angled edge of side wall 514. The control panel has a transverse dimension substantially less than the distance between side walls 514, 516 and is oriented at an angle toward rear wall 512 similar to that of the angled edge of sidewall 514. Projection 543 is substantially rectangular and is attached to front wall 510, a control panel lower section and side wall 516. The projection extends from the front wall toward the storage compartment for a slight distance and is oriented at an angle similar to that of control panel 541. The open area between control panel 541, side wall 516 and projection 543 defines the heating compartment open portion.

Storage compartment 506 is disposed above heating compartment 504 and includes a top wall 518, side walls 524, 526 and front and rear walls 528, 532 that collectively define the storage compartment interior. Front and rear walls 528, 532 are substantially rectangular and are attached to and extend between side walls 524, 526. Front wall 528 extends from the upper edges of door 530 and control panel 541, while rear wall 532 extends from and is integral with heating compartment rear wall 512. Side walls 524, 526 are substantially rectangular and are attached to and extend between respective side edges of front and rear walls 528, 532. The side walls respectively extend from and are integral with respective heating compartment side walls 514, 516.

Top wall 518 is substantially rectangular and is attached to the upper edges of the storage compartment front, rear and side walls. Top wall 518 further provides access to the storage compartment and is typically pivotally connected to rear wall 532. The top wall opens upward from the storage compartment to enable placement and removal of medical solution containers within the system. Door 530 is typically pivotally connected to the lower portion of front wall 528 and opens upward from the heating compartment in order to provide access to the heating compartment for placement and removal of medical solution containers within that compartment. Top wall 518 and door 530 may both be partially or completely transparent to allow viewing of the storage and heating compartment interiors, respectively. In addition, top wall 518 and/or door 530 may include any type of handle or latching mechanism to facilitate access to the system interior. The storage compartment basically houses additional medical solution containers to enable the system to accommodate and heat plural containers as described below.

Control panel 541 includes power switch 142 and controller 144 each as described above. The controller receives a desired temperature from a user and controls heating of a medical solution to attain that temperature in substantially the same manner described above. The heating compartment houses a heating assembly to uniformly apply heat to a medical solution. The heating assembly is substantially similar to the heating assembly described above and includes heating plate 150, heater 158 (FIG. 10), temperature sensor 172 and limit switch 160. The heating plate includes bottom wall 152 and side walls 154 extending at an angle from the bottom wall longer dimensioned side edges toward the interior surfaces of the heating compartment front and rear walls to form a generally 'U'-shaped heating plate configuration as described above. Heater 158 is disposed on the bottom surface of the heating plate bottom wall as described above. This arrangement facilitates rapid heating of a medical item as described above which is especially advantageous during employment of the system in time critical situations, such as in an operating room. For example, the system may heat items to a desired temperature in the approximate range of 80° F. to 150° F. within a short time interval, generally within one hour (e.g., the particular time interval depends on various factors, such as initial item temperature, room temperature, selected desired temperature, etc.). The limit switch includes arm 170 with temperature sensor 172, and housing 162 including support member 174, contact member 176 and switch circuitry 177 as described above. The limit switch is disposed below the heating plate with the limit switch components arranged in the manner described above for system 100. The limit switch detects the presence of a medical solution container on the heating plate and enables and disables heater 158 in substantially the same manner described above. Further, the limit switch arm may include cut-out switch 184 and/or additional temperature sensor 186 to facilitate disablement of the heater in response to excessive heater temperatures as described above. System 500 may include exemplary control circuitry 300 or 400 described above to control system operation.

Figure 10:
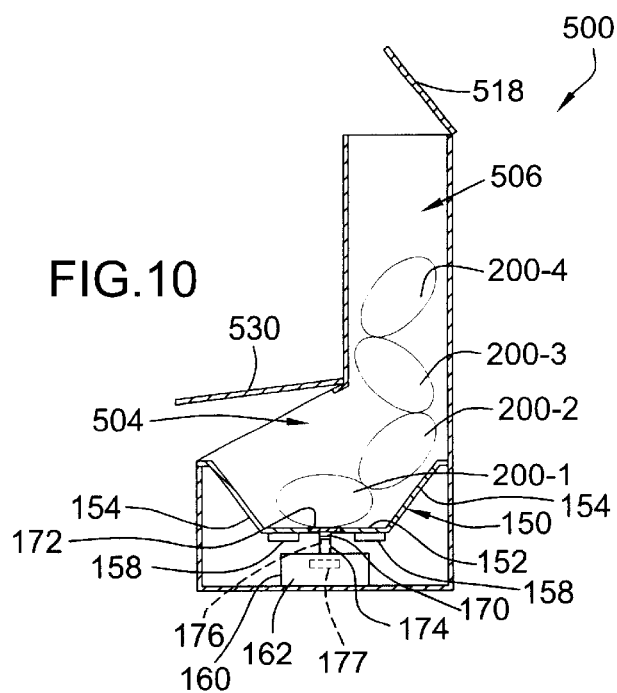
FIG. 10 is a side view in partial section of the system of FIG. 9.

System 500 stores and heats a plurality of medical solution containers as illustrated, by way of example only, in FIG. 10. Specifically, containers 200-1, 200-2, 200-3, 200-4 are initially placed into the system via top wall 518. The containers are typically positioned within the housing storage compartment in a stacked relation with each successive container placed within the storage compartment resting upon a previously loaded container. Typically, an initial container 200-1 is disposed on the heating plate bottom wall and in contact with temperature sensor 172. Container 200-1 is heated to a desired temperature entered by a user into controller 144 (FIG. 9). In response to attaining the desired temperature, container 200-1 is removed from the heating plate via door 530. After removal of container 200-1 from the heating compartment, successive container 200-2 is urged by gravitational forces, or may be manually manipulated, into position on the heating plate bottom wall for heating to the desired temperature. During switching of containers on the heating plate, the limit switch may momentarily disable the heater when the limit switch arm disengages with a container prior to engagement with another container. However, such momentary disablement does not significantly alter the desired temperature of the heating plate. Once the last container is removed from the system, the limit switch disables the heater until another container is placed on the heating plate as described above.

The alternative system provides the feature of heating plural medical solution containers simultaneously within the housing compartment. In particular, during heating of a container on the heating plate, remaining containers within the storage compartment are subjected to secondary heating prior to being received by the heating plate. Secondary heating occurs within the storage compartment as a result of convective heat transfer from the heating plate walls. A container subjected to secondary heating requires a shorter residence time on the heating plate to achieve the desired temperature, thereby accelerating the heating process.

Operation of system 500 is described with reference to FIGS. 9–10. Initially, operation of system 500 is substantially similar to the operation of system 100 described above except that additional containers may be stored within the storage compartment. Specifically, a user selects one or more medical solutions (e.g., bags or bottles containing saline or IV solutions, antibiotics or other drugs, blood, etc.) for heating by the system and determines an appropriate temperature for the solution. The user subsequently activates power switch 142 and pivots top wall 518 to an open state. The selected solution containers are placed into the system in stacked relation with an initial container disposed on heating plate 150 as described above.

Top wall 518 is subsequently pivoted to a closed state and the desired temperature for the selected solutions is entered into controller 144 via input devices or buttons 148 as described above. In response to placement of a container on the heating plate bottom wall, the container engages temperature sensor 172 and causes limit switch arm 170 to flex toward limit switch housing 162. The flexing of the limit switch arm forces contact member 176 into the limit switch housing to actuate switch circuitry 177 and effectively close the switch, thereby enabling heater 158 as described above. The controller receives signals from temperature sensor 172 and controls a solid state relay accordingly to enable or disable power to heater 158 as described above. The heater applies heat to the heating plate bottom wall, while heating plate side walls 154 conduct heat from bottom wall 152 to evenly distribute heat to the initial container. Cut-out switch 184 and/or temperature sensor 186 may be employed to facilitate disablement of the heater in response to excessive heater temperatures as described above.

In response to attaining the desired temperature, the initial container is removed from the heating plate via door 530, while a successive container is urged by gravitational forces and/or manually manipulated into position on the heating plate bottom wall. The above process may be repeated for subsequent containers stored in the system. Once the last container is removed, the limit switch disables the heater until another container is placed on the heating plate as described above.

It will be appreciated that the embodiments described above and illustrated in the drawings represent only a few of the many ways of implementing a medical solution warming system and method of heating and maintaining medical solutions at desired temperatures.

The system housings and housing components (e.g., panels, walls, etc.) maybe of any size, shape or configuration and may be constructed of any suitable materials including, but not limited to, electrogalvanized steel. The housing components may be connected via any conventional fastening techniques (e.g., welding, nuts and bolts, etc.). Any portion of the housings may be constructed of a transparent material. The heating, storage and housing compartments may be of any quantity, shape or size and may hold any quantity of medical solution containers or other items (e.g., one or more containers or items). The doors may be of any quantity, shape or size, may be constructed of any suitable materials, and may be connected to the housings at any suitable locations in any fashion to pivot in any desired direction and/or manner (e.g. hinged doors, sliding doors, removable panel doors, etc.). The alternative system top wall or other doors may be connected to the housing at any suitable locations in any fashion to pivot in any desired direction and/or manner (e.g. hinged doors, sliding doors, removable panel doors, etc.). Further, the doors and top wall may include a window of any size or shape, while the doors, top wall and/or window may be constructed of any translucent, transparent or other materials. The doors and top wall may include any quantity of any type of handle or latching mechanism disposed at any suitable locations. The housing open portions may be of any shape or size and may be disposed at any suitable locations. The housings may include any types of openings, mechanisms, devices or other techniques to provide access to the housing interior.

The systems may warm any quantity of any type of medical solution container or other item to any desired temperature. The controllers may be implemented by any conventional or other microprocessor, controller or circuitry performing the functions described above. The controllers may be disposed on or within the systems at any suitable locations. The controllers may control the heater to any desired temperature. The controllers may include any quantity of any type of input device (e.g., keys, buttons, mouse, voice, etc.) to facilitate entry of any desired temperatures or any other information. The controllers may include any quantity of any type of display of any shape or size to convey any desired information. The display may be integral with or detached from the controllers or systems and may include an LED or LCD display, indicator lights, or any other mechanism for indicating desired and/or measured temperature or any other information. Further, the display may include any type of buttons or data entry devices to program the controller in any manner. The controllers may employ any conventional or other control algorithms (e.g., fuzzy logic, PID, etc.). The systems may include any quantity of controllers to accommodate any quantity of heating assemblies, or a single controller may accommodate plural heating assemblies.

The heating plate may be of any quantity, shape, size or configuration to heat a medical solution or other item. The heating plate may include any quantity of conducting and/or non-conducting walls and may be constructed of any suitable materials. The heater maybe implemented by any quantity of any conventional heater or other heating device. The heating plate may include any quantity of heaters of any shape or size arranged in any configuration (e.g., strips, annular, segments, etc.) and disposed at any suitable locations for applying heat. The heater may be attached to the heating plate via any conventional or other fastening technique (e.g., pressure sensitive or other adhesives, etc.). The systems may alternatively include any quantity of heaters of any shape or size disposed at any suitable locations on the heating plate or within the systems.

The temperature sensors may be implemented by any quantity of any type of conventional or other temperature measuring device (e.g., RTD, infrared, etc.) and may be disposed at any suitable locations on the arm, heating plate or within the systems. The cut-out switch may be implemented by any quantity of any type of conventional or other limiting device and may be utilized for any desired temperature or threshold. The cut-out switch may be utilized in combination with the additional temperature sensor to facilitate disablement of the heater in response to any desired temperature or temperature range. The cut-out switch and/or additional sensor may be disposed at any locations on the arm, heating plate or within the systems and may measure the temperature of any system objects (e.g., heating plate, medical item, heater, etc.). Alternatively, a single temperature sensor may be employed to facilitate control of the heater in response to measured medical item and excessive heater temperatures.

The limit switch may be implemented by any quantity of any type of pressure or other switch and/or switch/sensor combination for detecting the presence of a medical solution container or other item and actuating or disabling a circuit. The limit switch may include any types of mechanical, electrical and/or chemical switching mechanisms or any combinations thereof. The limit switch may be positioned at any location proximate the heating plate or within the systems to detect the presence of a medical solution container or other item. The limit switch components (e.g., housing, arm, support member, contact member, etc.) may be of any shape or size and may be constructed of any suitable materials. The arm may support any quantity of any types of sensing devices. The switching circuitry may include any conventional or other circuitry or mechanical and/or electrical components that accommodate the contact member to establish or remove a circuit connection (e.g., open or close a circuit). The control circuits may utilize any conventional or other connectors or wiring to transfer power and other signals to system components. Further, the control circuit components (e.g., power switch, relay, fuses, controller, etc.) may be implemented by any quantity of any conventional or other electrical components arranged in any fashion and performing the functions described above. The circuits may be disposed at any location on or within the housings and may be arranged in any fashion to control heating of the heating plate as described above. The fuses may be implemented by any conventional or other fuses or limiting devices configured for any desired current level. The power switch and controllers may be disposed at any suitable locations on or within the housings.

The present invention systems may be used at any suitable locations (e.g., hospital or other medical facility, emergency medical or other vehicles, etc.) with any types of power sources (e.g., AC, DC, wall outlet jack, batteries, vehicle power system, etc.) to heat any quantity of any type of medical solution container or other item. The systems may be mounted on or supported by any type of support structure (e.g., wall, cart, table, floor, etc.). The systems preferably heat items to desired temperatures within the approximate range of 80° F.–150° F., but maybe utilized to heat the items to any desired temperatures or temperature ranges.

The present invention is not limited to the applications disclosed herein, but may be utilized to heat medical solutions or any other types of items (e.g., medical or other instruments, blankets, garments, containers, etc.) to any desired temperatures within any time interval (e.g., minutes hours, etc.). Further, the systems may be employed at any locations within operating rooms or other medical facilities or at any other desired sites.

From the foregoing description, it will be appreciated that the invention makes available a novel medical solution warming system and method of heating and maintaining medical solutions at desired temperatures, wherein a system housing includes a heating assembly with a generally U-shaped heating plate to evenly distribute heat to items placed thereon and a limit switch to enable a heater in response to a medical item being disposed on the heating plate.

Having described preferred embodiments of a new and improved medical solution warming system and method of heating and maintaining medical solutions at desired temperatures, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A temperature control system for heating medical items to desired temperatures comprising:
    a system housing;
    a heating compartment disposed within said housing to receive at least one medical item;
    a heating assembly disposed within said heating compartment to support and distribute heat to said at least one medical item placed thereon;
    a switching device to detect the presence of said at least one medical item on said heating assembly and to enable said heating assembly to heat said at least one medical item in response to said detection; and
    a controller to control a thermal output of said heating assembly to heat said at least one medical item to a desired temperature.

2. The temperature control system of claim 1, further including a temperature sensor to measure a temperature of said at least one medical item, wherein said controller facilitates entry of said desired temperature for said at least one medical item and controls said thermal output of said heating assembly to heat said at least one medical item to said entered desired temperature based on said temperature measured by said temperature sensor.

3. The temperature control system of claim 1, wherein said switching device autonomously enables said heating assembly when said at least one medical item is disposed on said heating assembly and autonomously disables said heating assembly when said at least one medical item is removed from said heating assembly.

4. The temperature control system of claim 1, wherein said switching device includes a sensing device to sense when said at least one medical item is disposed on said heating assembly.

5. The temperature control system of claim 1, wherein said switching device includes a pressure sensitive switch to sense when said at least one medical item is disposed on said heating assembly.

6. The temperature control system of claim 2, wherein said temperature sensor is disposed in proximity to said heating assembly to directly contact said at least one medical item disposed on said heating assembly.

7. The temperature control system of claim 2, wherein said temperature sensor is disposed on said switching device to directly contact said at least one medical item and to measure a temperature of said at least one medical item when said at least one medical item is disposed on said heating assembly.

8. The temperature control system of claim 1, wherein said heating assembly includes:
    a heating plate to support and distribute heat to said at least one medical item placed thereon, wherein said heating plate includes at least one primary conducting wall and at least one secondary conducting wall; and
    a heater affixed and applying heat to said heating plate, wherein said heater is attached to and covers selected portions of said at least one primary conducting wall to directly apply heat to said selected portions, wherein each said secondary conducting wall is coupled to said at least one primary conducting wall receiving said heater and receives said applied heat through conduction from said selected portions, and wherein said primary and secondary conducting walls distribute heat in a substantially uniform manner to said at least one medical item disposed on said heating plate.

9. The temperature control system of claim 8, wherein said heating plate includes a generally U-shaped configuration with said at least one primary conducting wall including a thermally conductive bottom wall and said at least one secondary conducting wall including a plurality of thermally conductive side walls extending from said bottom wall, and wherein said heater is affixed to said bottom wall.

10. The temperature control system of claim 9, wherein said switching device includes a flexible arm extending along an underside portion of said bottom wall, and said bottom wall includes an opening aligned with said flexible arm to allow an engaging portion of said flexible arm to extend through said opening to engage said at least one medical item when said at least one medical item is disposed on said heating plate.

11. The temperature control system of claim 10, wherein said flexible arm is movable in a direction away from said bottom wall to close said switching device and enable said heater when said at least one medical item engages said engaging portion of said flexible arm, and said flexible arm is resiliently biased toward said bottom wall to open said switching device and disable said heater when said at least one medical item is removed from said heating plate.

12. The temperature control system of claim 1, further including a storage compartment within said housing coupled to said heating compartment to receive and retain medical items to be heated.

13. The temperature control system of claim 12, further including:
a storage port to provide access to said storage compartment to facilitate insertion and removal of said medical items within said storage compartment; and
a heating port to provide access to said heating compartment to facilitate insertion and removal of said at least one medical item within said heating compartment.

14. A temperature control system for heating a medical item to a desired temperature comprising:
a system housing;
a heating compartment disposed within said housing to receive said medical item;
a heating assembly disposed within said heating compartment to heat said medical item, wherein said heating assembly includes:
a heating plate to support and distribute heat to said medical item placed thereon, wherein said heating plate includes at least one primary conducting wall and at least one secondary conducting wall oriented at an outward angle relative to said primary conducting wall; and
a heater affixed and applying heat to said heating plate, wherein said heater is attached to and covers selected portions of said at least one primary conducting wall to directly apply heat to said selected portions, wherein each said secondary conducting wall is coupled to said at least one primary conducting wall receiving said heater and receives said applied heat through conduction from said selected portions, and wherein said primary and secondary conducting walls distribute heat in a substantially uniform manner to said medical item disposed on said heating plate; and a controller to control a thermal output of said heater to heat said medical item to a desired temperature.

15. The temperature control system of claim 14, further including a temperature sensor to measure a temperature of said at least one medical item, wherein said controller facilitates entry of said desired temperature for said at least one medical item and controls said thermal output of said heater to heat said at least one medical item to said entered desired temperature based on said temperature measured by said temperature sensor.

16. The temperature control system of claim 14, further including a switching device to enable said heater in response to detection of the presence of said at least one medical item on said heating plate.

17. In a temperature control system including a system housing, a heating compartment disposed within said housing and a heating assembly disposed within said heating compartment, a method of heating medical items to desired temperatures comprising the steps of:
(a) receiving said at least one medical item on said heating assembly disposed within said heating compartment;
(b) detecting the presence of said at least one medical item on said heating assembly via a switching device and enabling said heating assembly to heat said at least one medical item in response to said detection; and
(c) controlling a thermal output of said heating assembly to heat said at least one medical item to a desired temperature.

18. The method of claim 17, wherein step (a) further includes:
(a.1) facilitating entry of said desired temperature for said at least one medical item; and
step (c) further includes:
(c.1) measuring a temperature of said at least one medical item; and
(c.2) controlling said thermal output of said heating assembly to heat said at least one medical item to said entered desired temperature based on said measured temperature.

19. The method of claim 17, wherein step (b) further includes:
(b.1) autonomously enabling said heating assembly when said at least one medical item is disposed on said heating assembly; and
(b.2) autonomously disabling said heating assembly when said at least one medical item is removed from said heating assembly.

20. The method of claim 17, wherein step (b) further includes:
(b.1) sensing when said at least one medical item is disposed on said heating assembly via a sensing device.

21. The method of claim 17, wherein step (b) further includes:
(b.1) sensing when said at least one medical item is disposed on said heating assembly via a pressure sensitive switch.

22. The method of claim 17, wherein step (c) further includes:
(c.1) measuring a temperature of said at least one medical item via a temperature sensor disposed in proximity to said heating assembly and in direct contact with said at least one medical item disposed on said heating assembly; and
(c.2) controlling said thermal output of said heating assembly to heat said at least one medical item to said desired temperature based on said measured temperature.

23. The method of claim 18, wherein step
(c.1) further includes:
(c.1.1) measuring said temperature of said at least one medical item when said at least one medical item is disposed on said heating assembly via a temperature sensor disposed on said switching device and in direct contact with said at least one medical item.

24. The method of claim 17, wherein said heating assembly includes a heating plate and a heater, and step (b) further includes:
(b.1) supporting and distributing heat to said at least one medical item placed on said heating plate, wherein said heating plate includes at least one primary conducting wall and at least one secondary conducting wall; and
(b.2) applying heat from said heater to said heating plate, wherein said heater is attached to and covers selected portions of said at least one primary conducting wall to directly apply heat to said selected portions, wherein each said secondary conducting wall is coupled to said at least one primary conducting wall receiving said heater and receives said applied heat through conduction from said selected portions, and wherein said primary and secondary conducting walls distribute heat in a substantially uniform manner to said at least one medical item disposed on said heating plate.

25. The method of claim 24, wherein step (b.1) further includes:
(b.1.1) supporting and distributing heat to said at least one medical item placed on said heating plate, wherein said heating plate includes a generally U-shaped configuration with said at least one primary conducting wall including a thermally conductive bottom wall and said at least one secondary conducting wall including a plurality of thermally conductive side walls extending from said bottom wall, and wherein said heater is affixed to said bottom wall.

26. The method of claim 17, wherein said temperature control system further includes a storage compartment within said housing coupled to said heating compartment, and step (a) further includes:
(a.1) receiving and retaining medical items to be heated within said storage compartment.

27. The method of claim 26, wherein said temperature control system further includes a storage port to provide access to said storage compartment and a heating port to provide access to said heating compartment, and step (a.1) further includes:
(a.1.1) facilitating insertion and removal of said medical items within said storage compartment via said storage port; and
(a.1.2) facilitating insertion and removal of said at least one medical item within said heating compartment via said heating port.

28. A temperature control system for heating medical items to desired temperatures comprising:
a system housing;
a heating compartment disposed within said housing to receive at least one medical item;
heating means disposed within said heating compartment for supporting and distributing heat to said at least one medical item placed thereon;
switching means for detecting the presence of said at least one medical item on said heating means and for enabling said heating means to heat said at least one medical item in response to said detection; and
control means for controlling a thermal output of said heating means to heat said at least one medical item to a desired temperature.

29. The temperature control system of claim 28, wherein said heating means includes:
heat distribution means for supporting and distributing heat to said at least one medical item placed thereon, wherein said heat distribution means includes at least one primary conducting wall and at least one secondary conducting wall; and
heat supply means affixed and for applying heat to said heat distribution means, wherein said heat supply means is attached to and covers selected portions of said at least one primary conducting wall to directly apply heat to said selected portions, wherein each said secondary conducting wall is coupled to said at least one primary conducting wall receiving said heat supply means and receives said applied heat through conduction from said selected portions, and wherein said primary and secondary conducting walls distribute heat in a substantially uniform manner to said at least one medical item disposed on said heat distribution means.

30. The temperature control system of claim 28, further including a storage compartment within said housing coupled to said heating compartment to receive and retain medical items to be heated.

31. The temperature control system of claim 28, wherein said desired temperature is within an approximate temperature range of 80° F. to 150° F. and said heating means heats said at least one medical item to said desired temperature within a one hour time interval.

32. The temperature control system of claim 28, further including temperature sensing means for measuring a temperature of said at least one medical item, wherein said control means facilitates entry of said desired temperature for said at least one medical item and controls said thermal output of said heating means to heat said at least one medical item to said entered desired temperature based on said temperature measured by said temperature sensing means.

33. The temperature control system of claim 32, wherein said temperature sensing means is disposed on said switching means to directly contact said at least one medical item and to measure a temperature of said at least one medical item when said at least one medical item is disposed on said heating means.

34. The temperature control system of claim 32, further including limit switching means for measuring a temperature associated with said heating means and disabling said heating means when said temperature measured by said limit switching means exceeds a predetermined threshold.

35. The temperature control system of claim 32, further including limit temperature means for measuring a temperature associated with said heating means, wherein said control means disables said heating means when said temperature measured by said limit temperature means exceeds a predetermined threshold.

36. The temperature control system of claim 1, wherein said desired temperature is within an approximate temperature range of 80° F. to 150° F. and said heating assembly heats said at least one medical item to said desired temperature within a one hour time interval.

37. The temperature control system of claim 2, further including a limit switching device to measure a temperature associated with said heating assembly and disable said heating assembly when said temperature measured by said limit switching device exceeds a predetermined threshold.

38. The temperature control system of claim 2, further including a limit temperature sensor to measure a temperature associated with said heating assembly, wherein said controller disables said heating assembly when said temperature measured by said limit temperature sensor exceeds a predetermined threshold.

39. A temperature control system for heating medical items to desired temperatures comprising:
a system housing;
a heating compartment disposed within said housing to receive at least one medical item;
a heating assembly disposed within said heating compartment to heat said at least one medical item, wherein said heating assembly includes:
a heating plate to support and distribute heat to said at least one medical item placed thereon, wherein said heating plate includes at least one primary conducting wall and at least one secondary conducting wall; and
a heater affixed and applying heat to said heating plate, wherein said heater is attached to and covers selected portions of said at least one primary conducting wall to directly apply heat to said selected portions, wherein each said secondary conducting wall is coupled to said at least one primary conducting wall receiving said heater and receives said applied heat through conduction from said selected portions, and wherein said primary and secondary conducting walls distribute heat in a substantially uniform manner to said at least one medical item disposed on said heating plate; and
a controller to control a thermal output of said heater to heat said at least one medical item to a desired temperature, wherein said desired temperature is within an approximate temperature range of 80° F. to 150° F. and said heating assembly heats said at least one medical item to said desired temperature within a one hour time interval.

40. The temperature control system of claim 15, further including a limit switching device to measure a temperature associated with said heater and disable said heater when said temperature measured by said limit switching device exceeds a predetermined threshold.

41. The temperature control system of claim 15, further including a limit temperature sensor to measure a temperature associated with said heater, wherein said controller disables said heater when said temperature measured by said limit temperature sensor exceeds a predetermined threshold.

42. The method of claim 17, wherein said desired temperature is within an approximate temperature range of 80° F. to 150° F., and step (c) further includes:
(c.1) controlling said thermal output of said heating assembly to heat said at least one medical item to said desired temperature within a one hour time interval.

43. The method of claim 18, wherein step (c.1) further includes:
(c.1.1) measuring a temperature associated with said heating assembly; and step (c.2) further includes:
(c.2.1) disabling said heating assembly when said temperature associated with said heating assembly exceeds a predetermined threshold.

44. A temperature control system for heating medical items to desired temperatures within an operating room comprising:
a system housing configured for placement within said operating room;
a heating compartment disposed within said housing to receive at least one medical item;
a heating assembly disposed within said heating compartment to support and distribute heat to said at least one medical item placed thereon; and
a controller to control a thermal output of said heating assembly to heat said at least one medical item within said operating room to a desired temperature within a one hour time interval, wherein said desired temperature resides within an approximate range of 80° F. to 150° F.

45. The temperature control system of claim 44, further including a switching device to enable said heating assembly to heat said at least one medical item in response to detection of the presence of said at least one medical item on said heating assembly.

46. The temperature control system of claim 44, wherein said heating assembly includes:
a heating plate to support and distribute heat to said at least one medical item placed thereon, wherein said heating plate includes at least one primary conducting wall and at least one secondary conducting wall; and
a heater affixed and applying heat to said heating plate, wherein said heater is attached to and covers selected portions of said at least one primary conducting wall to directly apply heat to said selected portions, wherein each said secondary conducting wall is coupled to said at least one primary conducting wall receiving said heater and receives said applied heat through conduction from said selected portions, and wherein said primary and secondary conducting walls distribute heat in a substantially uniform manner to said at least one medical item disposed on said heating plate.

47. The temperature control system of claim 44, further including a storage compartment within said housing coupled to said heating compartment to receive and retain medical items to be heated.

48. The temperature control system of claim 44, further including a temperature sensor to measure a temperature of said at least one medical item, wherein said controller facilitates entry of said desired temperature for said at least one medical item and controls said thermal output of said heating assembly to heat said at least one medical item to said entered desired temperature based on said temperature measured by said temperature sensor.

49. The temperature control system of claim 48, further including a switching device to enable said heating assembly to heat said at least one medical item in response to detection of the presence of said at least one medical item on said heating assembly;
wherein said temperature sensor is disposed on said switching device to directly contact said at least one medical item and to measure a temperature of said at least one medical item when said at least one medical item is disposed on said heating assembly.

50. The temperature control system of claim 48, further including a limit switching device to measure a temperature associated with said heating assembly and disable said heating assembly when said temperature measured by said limit switching device exceeds a predetermined threshold.

51. The temperature control system of claim 48, further including a limit temperature sensor to measure a temperature associated with said heating assembly, wherein said controller disables said heating assembly when said temperature measured by said limit temperature sensor exceeds a predetermined threshold.

52. In a temperature control system including a system housing configured for placement within an operating room, a heating compartment disposed within said housing and a heating assembly disposed within said heating compartment, a method of heating medical items to desired temperatures within said operating room comprising the steps of:

(a) receiving said at least one medical item on said heating assembly disposed within said heating compartment; and (b) controlling a thermal output of said heating assembly to heat said at least one medical item within said operating room to a desired temperature within a one hour time interval, wherein said desired temperature resides within an approximate range of 80° F. to 150° F.

53. The method of claim 52, wherein step (b) further includes:

(b.1) enabling said heating assembly to heat said at least one medical item in response to detection of the presence of said at least one medical item on said heating assembly.

54. The method of claim 52, wherein said heating assembly includes a heating plate and a heater, and step (b) further includes:

(b.1) supporting and distributing heat to said at least one medical item placed on said heating plate, wherein said heating plate includes at least one primary conducting wall and at least one secondary conducting wall; and (b.2) applying heat from said heater to said heating plate, wherein said heater is attached to and covers selected portions of said at least one primary conducting wall to directly apply heat to said selected portions, wherein each said secondary conducting wall is coupled to said at least one primary conducting wall receiving said heater and receives said applied heat through conduction from said selected portions, and wherein said primary and secondary conducting walls distribute heat in a substantially uniform manner to said at least one medical item disposed on said heating plate.

55. The method of claim 52, wherein said temperature control system further includes a storage compartment within said housing coupled to said heating compartment, and step (a) further includes:

(a.1) receiving and retaining medical items to be heated within said storage compartment.

56. The method of claim 52, wherein step (a) further includes:

(a.1) facilitating entry of said desired temperature for said at least one medical item; and step (b) further includes:

(b.1) measuring a temperature of said at least one medical item; and (b.2) controlling said thermal output of said heating assembly to heat said at least one medical item to said entered desired temperature based on said measured temperature.

57. The method of claim 56, wherein step (b.2) further includes:

(b.2.1) enabling said heating assembly to heat said at least one medical item, via a switching device, in response to detection of the presence of said at least one medical item on said heating assembly; and (b.2.2) measuring said temperature of said at least one medical item when said at least one medical item is disposed on said heating assembly via a temperature sensor disposed on said switching device and in direct contact with said at least one medical item.

58. The method of claim 56, wherein step (b.2) further includes:

(b.2.1) measuring a temperature associated with said heating assembly via a limit switching device; and (b.2.2) disabling said heating assembly when said temperature associated with said heating assembly exceeds a predetermined threshold.

59. The method of claim 56, wherein step (b.2) further includes:

(b.2.1) measuring a temperature associated with said heating assembly via a limit temperature sensor; and (b.2.2) disabling said heating assembly when said temperature associated with said heating assembly exceeds a predetermined threshold.

60. A temperature control system for heating medical items to desired temperatures within an operating room comprising:

a system housing configured for placement within said operating room;

a heating compartment disposed within said housing to receive at least one medical item;

heating means disposed within said heating compartment for supporting and distributing heat to said at least one medical item placed thereon; and control means for controlling a thermal output of said heating means to heat said at least one medical item within said operating room to a desired temperature within a one hour time interval, wherein said desired temperature resides within an approximate range of 80° F. to 150° F.

61. The temperature control system of claim 60, further including switching means to enable said heating means to heat said at least one medical item in response to detection of the presence of said at least one medical item on said heating means.

62. The temperature control system of claim 60, wherein said heating means includes:

heat distribution means for supporting and distributing heat to said at least one medical item placed thereon, wherein said heat distribution means includes at least one primary conducting wall and at least one secondary conducting wall; and heat supply means affixed and for applying heat to said heat distribution means, wherein said heat supply means is attached to and covers selected portions of said at least one primary conducting wall to directly apply heat to said selected portions, wherein each said secondary conducting wall is coupled to said at least one primary conducting wall receiving said heat supply means and receives said applied heat through conduction from said selected portions, and wherein said primary and secondary conducting walls distribute heat in a substantially uniform manner to said at least one medical item disposed on said heat distribution means.

63. The temperature control system of claim 60, further including a storage compartment within said housing coupled to said heating compartment to receive and retain medical items to be heated.

64. The temperature control system of claim 60, further including temperature sensing means for measuring a temperature of said at least one medical item, wherein said control means facilitates entry of said desired temperature for said at least one medical item and controls said thermal output of said heating assembly to heat said at least one medical item to said entered desired temperature based on said temperature measured by said temperature sensing means.

65. The temperature control system of claim 64, further including switching means for enabling said heating means to heat said at least one medical item in response to detection of the presence of said at least one medical item on said heating means;

wherein said temperature sensing means is disposed on said switching means to directly contact said at least one medical item and to measure a temperature of said at least one medical item when said at least one medical item is disposed on said heating means.

66. The temperature control system of claim 64, further including limit switching means for measuring a temperature associated with said heating means and disabling said heating means when said temperature measured by said limit switching means exceeds a predetermined threshold.

67. The temperature control system of claim 64, further including limit temperature means for measuring a temperature associated with said heating means, wherein said control means disables said heating means when said temperature measured by said limit temperature means exceeds a predetermined threshold.

68. A temperature control system for heating medical items to desired temperatures comprising:

a system housing;

a heating compartment disposed within said housing to receive at least one medical item;

a heating assembly disposed within said heating compartment to support and distribute heat to said at least one medical item placed thereon;

a temperature sensor to contact said at least one medical item place on said heating assembly and to measure a temperature of said at least one medical item;

a limit temperature sensor to measure a temperature associated with said heating assembly; and a controller to facilitate entry of said desired temperature for said at least one medical item and to control a thermal output of said heating assembly to heat said at least one medical item to said entered desired temperature based on said temperature measured by said temperature sensor, wherein said controller disables said heating assembly when said temperature measured by said limit temperature sensor exceeds a predetermined threshold.

69. The temperature control system of claim 68, further including a switching device to enable said heating assembly to heat said at least one medical item in response to detection of the presence of said at least one medical item on said heating assembly.

70. The temperature control system of claim 69, wherein at least one of said temperature sensor and said limit temperature sensor are disposed on said switching device.

71. The temperature control system of claim 68, wherein said heating assembly includes:

a heating plate to support and distribute heat to said at least one medical item placed thereon, wherein said heating plate includes at least one primary conducting wall and at least one secondary conducting wall; and a heater affixed and applying heat to said heating plate, wherein said heater is attached to and covers selected portions of said at least one primary conducting wall to directly apply heat to said selected portions, wherein each said secondary conducting wall is coupled to said at least one primary conducting wall receiving said heater and receives said applied heat through conduction from said selected portions, and wherein said primary and secondary conducting walls distribute heat in a substantially uniform manner to said at least one medical item disposed on said heating plate.

72. The temperature control system of claim 68, further including a storage compartment within said housing coupled to said heating compartment to receive and retain medical items to be heated.

73. A temperature control system for heating medical items to desired temperatures comprising:

a system housing;

a heating compartment disposed within said housing to receive at least one medical item;

a heating assembly disposed within said heating compartment to support and distribute heat to said at least one medical item placed thereon;

a temperature sensor to measure a temperature of said at least one medical item;

a limit temperature sensor to measure a temperature associated with said heating assembly; and a controller to facilitate entry of said desired temperature for said at least one medical item and to control a thermal output of said heating assembly to heat said at least one medical item to said entered desired temperature based on said temperature measured by said temperature sensor, wherein said controller disables said heating assembly when said temperature measured by said limit temperature sensor exceeds a predetermined threshold;

wherein said desired temperature is within an approximate temperature range of 80° F. to 150° F. and said heating assembly heats said at least one medical item to said desired temperature within a one hour time interval.

74. In a temperature control system including a system housing, a heating compartment disposed within said housing and a heating assembly disposed within said heating compartment, a method of heating medical items to desired temperatures comprising the steps of:

(a) receiving said at least one medical item on said heating assembly disposed within said heating compartment and facilitating entry of said desired temperature for said at least one medical item;

(b) measuring a temperature of said at least one medical item via a temperature sensor that contacts said at least one medical item;

(c) measuring a temperature associated with said heating assembly via a limit temperature sensor; and (d) controlling a thermal output of said heating assembly to heat said at least one medical item to said entered desired temperature based on said temperature measured by said temperature sensor and disabling said heating assembly when said temperature measured by said limit temperature sensor exceeds a predetermined threshold.

75. The method of claim 74, wherein step (d) further includes:

(d.1) enabling said heating assembly to heat said at least one medical item in response to detection of the presence of said at least one medical item on said heating assembly.

76. The method of claim 74, wherein said heating assembly includes a heating plate and a heater, and step (d) further includes:

(d.1) supporting and distributing heat to said at least one medical item placed on said heating plate, wherein said heating plate includes at least one primary conducting wall and at least one secondary conducting wall; and (d.2) applying heat from said heater to said heating plate, wherein said heater is attached to and covers selected portions of said at least one primary conducting wall to directly apply heat to said selected portions, wherein each said secondary conducting wall is coupled to said at least one primary conducting wall receiving said heater and receives said applied heat through conduction from said selected portions, and wherein said primary and secondary conducting walls distribute heat in a substantially uniform manner to said at least one medical item disposed on said heating plate.

77. The method of claim 74, wherein said temperature control system further includes a storage compartment within said housing coupled to said heating compartment, and step (a) further includes:
   (a.1) receiving and retaining medical items to be heated within said storage compartment.

78. In a temperature control system including a system housing, a heating compartment disposed within said housing and a heating assembly disposed within said heating compartment, a method of heating a medical item to a desired temperature comprising the steps of:
   (a) receiving said at least one medical item on said heating assembly disposed within said heating compartment and facilitating entry of said desired temperature for said at least one medical item;
   (b) measuring a temperature of said at least one medical item via a temperature sensor;
   (c) measuring a temperature associated with said heating assembly via a limit temperature sensor; and
   (d) controlling a thermal output of said heating assembly to heat said at least one medical item to said entered desired temperature based on said temperature measured by said temperature sensor and disabling said heating assembly when said temperature measured by said limit temperature sensor exceeds a predetermined threshold; wherein said desired temperature is within an approximate temperature range of 80° F. to 150° F., and step (d) further includes:
      (d.1) controlling said thermal output of said heating assembly to heat said at least one medical item to said desired temperature within a one hour time interval.

79. A temperature control system for heating medical items to desired temperatures comprising:
   a system housing;
   a heating compartment disposed within said housing to receive at least one medical item;
   heating means disposed within said heating compartment for supporting and distributing heat to said at least one medical item placed thereon;
   temperature sensing means for contacting said at least one medical item placed on said heating means and for measuring a temperature of said at least one medical item;
   limit temperature means for measuring a temperature associated with said heating means; and
   control means for facilitating entry of said desired temperature for said at least one medical item and for controlling a thermal output of said heating means to heat said at least one medical item to said entered desired temperature based on said temperature measured by said temperature sensing means, wherein said control means disables said heating means when said temperature measured by said limit temperature means exceeds a predetermined threshold.

80. The temperature control system of claim 79, further including switching means for enabling said heating means to heat said at least one medical item in response to detection of the presence of said at least one medical item on said heating means.

81. The temperature control system of claim 80, wherein at least one of said temperature sensing means and said limit temperature means are disposed on said switching means.

82. The temperature control system of claim 79, wherein said heating means includes:
   heat distribution means for supporting and distributing heat to said at least one medical item placed thereon, wherein said heat distribution means includes at least one primary conducting wall and at least one secondary conducting wall; and
   heat supply means affixed and for applying heat to said heat distribution means, wherein said heat supply means is attached to and covers selected portions of said at least one primary conducting wall to directly apply heat to said selected portions, wherein each said secondary conducting wall is coupled to said at least one primary conducting wall receiving said heat supply means and receives said applied heat through conduction from said selected portions, and wherein said primary and secondary conducting walls distribute heat in a substantially uniform manner to said at least one medical item disposed on said heat distribution means.

83. The temperature control system of claim 79, further including a storage compartment within said housing coupled to said heating compartment to receive and retain medical items to be heated.

84. A temperature control system for heating medical items to desired temperatures comprising:
   a system housing;
   a heating compartment disposed within said housing to receive at least one medical item;
   heating means disposed within said heating compartment for supporting and distributing heat to said at least one medical item placed thereon;
   temperature sensing means for measuring a temperature of said at least one medical item;
   limit temperature means for measuring a temperature associated with said heating means; and
   control means for facilitating entry of said desired temperature for said at least one medical item and for controlling a thermal output of said heating means to heat said at least one medical item to said entered desired temperature based on said temperature measured by said temperature sensing means, wherein said control means disables said heating means when said temperature measured by said limit temperature means exceeds a predetermined threshold; and wherein said desired temperature is within an approximate temperature range of 80° F. to 150° F. and said heating means heats said at least one medical item to said desired temperature within a one hour time interval.

85. In a temperature control system for heating a medical item to a desired temperature including a system housing, a heating compartment disposed within said housing, a heating assembly disposed within said heating compartment and including a heating plate and a heater, and a controller for controlling the heating assembly, wherein the heating plate includes at least one primary conducting wall and at least one secondary conducting wall oriented at an outward angle relative to said primary conducting wall, a method of heating a medical item to a desired temperature comprising the steps of:
   (a) receiving at least one medical item on said heating assembly disposed within said heating compartment;

(b) facilitating entry of said desired temperature for said medical item via said controller;

(c) applying heat directly to said at least one primary conducting wall of said heating plate via said heater attached to and covering selected portions of said at least one primary conducting wall;

(d) conducting said applied heat from said at least one primary conducting wall to said at least one secondary conducting wall, wherein said at least one secondary conducting wall is coupled to said at least one primary conducting wall at a location outside said selected portions, and wherein said at least one secondary conducting wall is oriented at an outward angle relative to said at least one primary conducting wall;

(e) distributing heat in a substantially uniform manner to said at least one medical item via said primary and secondary conducting walls; and (f) controlling a thermal output of said heating assembly to heat said at least one medical item to said entered desired temperature.

86. The method of claim 85, wherein step (f) further includes:

(f.1) measuring a temperature of said medical item via a temperature sensor; and (f.2) controlling said thermal output of said heating assembly to heat said at least one medical item to said entered desired temperature based on said measured temperature.

87. The method of claim 86, wherein step (f.1) further includes:

(f.1.1) measuring a temperature associated with said heater via a limit switching device; and step (f.2) further includes:

(f.2.1) disabling said heater when said temperature measured by said limit switching device exceeds a predetermined threshold.

88. The method of claim 86, wherein step (f.1) further includes:

(f.1.1) measuring a temperature associated with said heater via a limit temperature sensor; and step (f.2) further includes:

(f.2.1) disabling said heater via said controller when said temperature measured by said limit temperature sensor exceeds a predetermined threshold.

89. The method of claim 85, wherein step (f) further includes:

(f.1) detecting the presence of said medical item on said heating assembly via a switching device and enabling said heating assembly to heat said medical item in response to said detection.

90. In a temperature control system for heating a medical item to a desired temperature including a system housing, a heating compartment disposed within said housing, a heating assembly disposed within said heating compartment and including a heating plate and a heater, and a controller for controlling the heating assembly, wherein the heating plate includes at least one primary conducting wall and at least one secondary conducting wall, a method of heating a medical item to a desired temperature comprising the steps of:

(a) receiving at least one medical item on said heating assembly disposed within said heating compartment (b) facilitating entry of said desired temperature for said medical item via said controller;

(c) applying heat directly to said at least on primary conducting wall of said heating plate via said heater attached to and covering selected portions of said at least one primary conducting wall;

(d) conducting said applied heat from said at least one primary conducting wall to said at least one secondary conducting wall, wherein said at least one secondary conducting wall is coupled to said at least one primary conducting wall at a location outside said selected portions;

(e) distributing heat in a substantially uniform manner to said at least one medical item via said primary and secondary conducting walls; and (f) controlling a thermal output of said heating assembly to heat said at least one medical item to said entered desired temperature within a one hour time interval, wherein said desired temperature is within an approximate temperature range of 80° F. to 150° F.

* * * * *